United States Patent [19]

Poetsch et al.

[11] Patent Number: 4,837,402
[45] Date of Patent: Jun. 6, 1989

[54] PROCESS FOR THE PREPARATION OF D-(+)-BIOTIN

[75] Inventors: Eike Poetsch, Mühltal; Michael Casutt, Pfungstadt, both of Fed. Rep. of Germany

[73] Assignee: Merck Patent Gesellschaft Mit Beschränkter Haftung, Darmstadt, Fed. Rep. of Germany

[21] Appl. No.: 141,161

[22] Filed: Jan. 6, 1988

Related U.S. Application Data

[62] Division of Ser. No. 39,342, Apr. 17, 1987, Pat. No. 4,732,987.

[30] Foreign Application Priority Data

Apr. 19, 1986 [DE] Fed. Rep. of Germany ....... 3613245
Feb. 7, 1987 [DE] Fed. Rep. of Germany ....... 3703872

[51] Int. Cl.⁴ ............................................. C07D 495/04
[52] U.S. Cl. ...................................................... 548/303
[58] Field of Search .......................................... 548/303

[56] References Cited

U.S. PATENT DOCUMENTS 4,468,516  8/1984  Volkmann ...................... 548/303 X

*Primary Examiner*—Richard A. Schwartz
*Attorney, Agent, or Firm*—Millen & White

[57] ABSTRACT

D-(+)-Biotin can be prepared from optically active hydantoins of the formula I

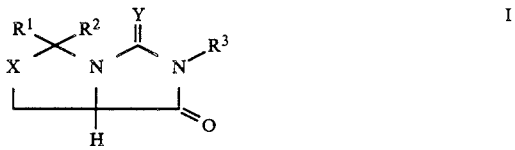

wherein $R^1$, $R^2$, $R^3$, X and Y have the meaning given in patent claim 1, in a simple, stereospecific manner.

Furthermore bicyclic nitriles of the formula XI

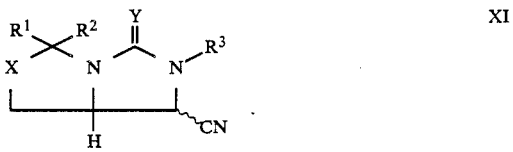

wherein $R^1$, $R^2$, $R^3$, X and Y have the meaning given represent precious intermediate products and educts of a multitude of possibilities to synthesize optically active D-(+)-biotin.

11 Claims, No Drawings

PROCESS FOR THE PREPARATION OF D-(+)-BIOTIN

This application is a division of application Ser. No. 039,342, filed Apr. 17, 1987, now U.S. Pat. No. 4,732,987.

BACKGROUND OF THE INVENTION

This application is copending with application Ser. No. 039,341, filed Apr. 17, 1987. The invention relates to a process for the preparation of D-(+)-biotin from L-cysteine or L-cystine or L-serine via an optically active (7R)-1H,3H-imidazol[1,5-c]azole as an intermediate product.

The invention was based on the object of providing a new process for the preparation of optically active D-(+)-biotin which avoids the procedure of racemate resolution and hence the discarding or recycling of the undesired enantiomer.

Upon further study of the specification and appended claims, further objects and advantages of this invention will become apparent to those skilled in the art.

Processes for the stereospecific synthesis of D-(+)-biotin from sugars of suitable configuration are known. Thus, D-mannose is used as the starting material in Tetrahedron Letters No. 32, pages 2765–2766 (1975), D-glucose is used as the starting material in Agric. Biol. Chem. No. 42, Page 465 (1978), and D-arabinose is used as the chiral starting material in German Offenlegungsschrift 3,122,562 and German Offenlegungsschrift 3,320,140.

All these processes are characterized, however, by a high number of synthesis steps with consequently a low overall yield. The intermediate stages, which usually cannot be crystallized because of their sugar nature, are frequently obtained only in unsatisfactory purity, and because of their polyfunctionality and the associated chemical instability, require observance of comparatively narrow reaction parameters. A number of sugars are also inaccessible from natural sources, which results in a high price.

The use of L-cysteine, such as is known from U.S. Pat. No. 4,009,172, U.S. Pat. No. 4,130,713, U.S. Pat. No. 4,337,345 and Journal of the American Chemical Society No. 99, page 7020 (1977), indeed avoids handling of unstable intermediate stages, but in constrast leads to only an unsatisfactory yield of optically active D-(+)-biotin by a total of 18 reaction stages with removal of undesired isomers.

In another process, substituted 3H,5H-imidazol[1,5-c]-tetrahyrothiazoles from which optically active biotin is obtained after racemate resolution are described in Journal of the American Chemical Society No. 105, Page 5946 (1983) and in European Published Application 0,094,776.

Since the comparatively high number of stages associated with in some cases moderate yields and the need for optical resolution also makes these starting substances to be poorly suitable for the preparation of D-(+)-biotin, there continued to be a need for a suitable process for simple economic stereospecific preparation of D-(+)-biotin.

SUMMARY OF THE INVENTION

The invention was based on the object of providing a new process for the preparation of optically active D-(+)-biotin which avoids the procedure of racemate resolution and hence the discarding or recycling of the undesired enantiomer.

Upon further study of the specification and appended claims, further objects and advantages of this invention will become apparent to those skilled in the art.

It has been found, surprisingly, that D-(+)-biotin can be prepared from the naturally occurring amino acids L-cysteine or L-cystine or L-serine via an optically active (7R)-1H,3H-imidazo[1,5-c]azole of the formula I as the intermediate product in a stereospecific manner without additional racemate resolution.

These objects therefore are satisfied by provision of a process for the preparation of D-(+)-biotin from L-cysteine or L-cystine or L-serine, characterized in that the synthesis is carried out via an intermediate product of the formula I

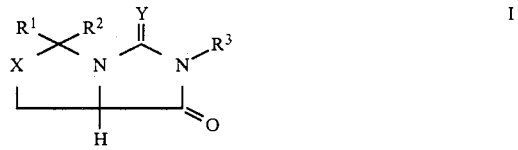

wherein
- $R^1$ and $R^2$ are each independently of one another H, unsubstituted or substituted alkyl, cycloalkyl, aryl, aralkyl or heteroaryl taken together are unsubstituted or substituted alkylene or heteroalkalene.
- $R^3$ is H or a protective group which is suitable for a nitrogen atom and
- X and Y independently of one another are each O or S.

DETAILED DISCUSSION

In this formula, X is preferably S and Y is preferably O, and in particular X=S and Y=O at the same time. The radicals $R^1$ and $R^2$ are preferably H, $C_1$–$C_4$-alkyl, or phenyl or benzyl which is unsubstituted or mono or polysubstituted by $C_1$–$C_3$-alkyl and/or alkoxy, and in particular $R^1$=H and $R^2$=phenyl at the same time. The radical $R^3$ is preferably benzyl which is unsutstituted or substituted by one or more, particularly preferably one or two, $C_1$–$C_4$-alkyl and/or $C_1$–$C_4$-alkoxy groups, in particular unsubstituted benzyl, and in addition also $C_3$–$C_5$-alk-2-enyl or $C_3$–$C_6$-trialkylsilyl. In the case of polysubstitution, preferably disubstitution, of a phenyl ring, the substituents are preferably identical, but can also be different. They are preferably in the 4- and/or 2-position, but can also be in the 3-, 5- and/or 6-position.

Generally, the alkyl portions have at least 1 C atom, the aryl portions 6–10 C atoms, the cycloalkyl portions at least 5 C atoms and the heteroaryl groups are of 1–3 rings, 4–6 atoms total in each ring and 0, 1 or 2 hetero O, N or S atoms in each ring, there typically being 1–4 hetero atoms in total. Heteroalkylene refers to alkylene groups wherein 1–3 methylene groups may be replaced by oxygen, sulfur or nitrogen.

The invention accordingly relates in particular to a process for the preparation of D-(+)-biotin from L-cysteine or L-cystine or L-serine via an intermediate product of the formula in which at least one of the radicals mentioned has one of the above-mentioned preferred meanings.

The invention furthermore relates to a process for the preparation of the optically active hydantoins of the formula I, characterized in that L-cysteine or LK-serine is reacted with an alkali metal cyanate or thiocyanate or alkaline earth metal cyanate or thiocyanate to give hydantoin of the formula II

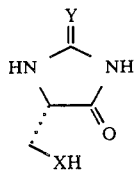
II wherein X and Y have the meaning given, this product is reacted with a carbonyl compound of the formula III $R^1—CO—R^2$    III wherein $R^1$ and $R^2$ have the meaning given, water being split off, to give a bicyclic compound of the formula IV

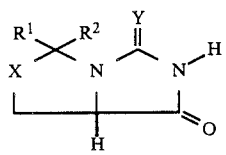
IV wherein $R^1$, $R^2$, X and Y have the meaning given, and the secondary nitrogen atom thereof is provided with a protective group $R^3$ of the meaning given, or in that L-cysteine or L-serine is reacted with a carbonyl compound of the formula III with the meaning given, water being split off, to give an azolidine V

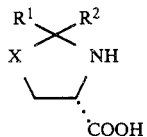
V wherein $R^1$, $R^2$ and X have the meaning given, this is reacted with a metal cyanate or thiocyanate to give a compound of the formula IV, and the subsequent procedure is as described above, or V is reacted with an organiisocyanate of isothiocyanate of the formula VI $R^3—N=C=Y$    VI wherein $R^3$ and Y have the meaning given to produce a compound of the formula I, or in that L-cystine is reacted with an alkali metal cyanate or thiocyanate or alkaline earth metal cyanate or thiocyanate to give a bis-hydantoin of the formula VII

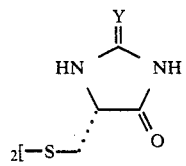
VII wherein Y is O or S, this is converted into a hydantoin of the formula II with a reducing agent and the product II is further reacted as described above, or its nitrogen atom in the 3-position is provided with a protective group $R^3$ of the meaning given and the resulting bis-hydantoin of the formula VIII

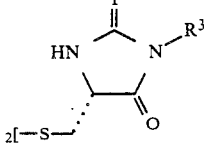
VIII wherein $R^3$ and Y have the meaning given, after cleavage by a reducing agent, is reacted with a carbonyl compound of the formula III, or in that L-cystine is reacted with an organoisocyanate or -isothiocyanate of the formula VI given to give a bis-hydantoin of the formula VIII and the subsequent procedure is as described above.

The present invention furthermore relates to a process for the preparation of D-(+)-biotin from compounds of the formula I, by a procedure in which
(a) I is reduced to an alcohol of the formula IX

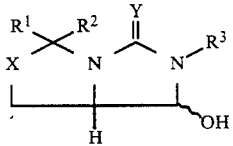
IX wherein $R^1$, $R^2$, $R^3$, X and Y have the meaning given, this is converted into an activated ester of the formula X

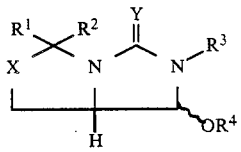
X wherein $R^1$, $R^2$, $R^3$, X and Y have the meaning given and the radical $R^4$ is an activating ester group. This compound is reacted with an alkali metal cyanate or a cyanosilane or alkaline earth metal cyanide to give a nitrile of the formula XI

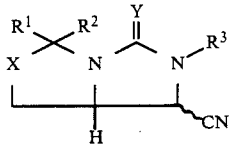
XI wherein $R^1$, $R^2$, $R^3$, X and Y have the meaning given, this is reacted with a base or an acid to give an acid derivative of the formula XII

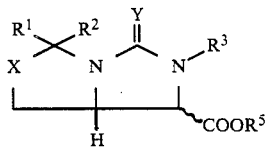
XII wherein $R^1$, $R^2$, $R^3$, X and Y have the meaning given and $R^5$ is H, lower alkyl, cycloalkyl or aryl, this is cyclized water being split off, to give a lactone of the formula XIII

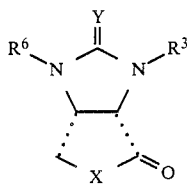

XIII wherein $R^3$, X and Y have the meaning given and $R^6$ is H or $R^1R^2CH$, this is converted by known processes into D-(+)-biotin, or by a procedure in which (b) XI is reacted with an organometallic compound to give an oxo compound of the formula XIV

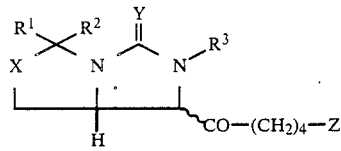

XIV wherein $R^1$, $R^2$, $R^3$, X and Y have the meaning given and Z is $OR^5$ or $COOR^5$, this is split by treatment with an acid and/or a reducing agent to give an imidazolidine of the formula XV

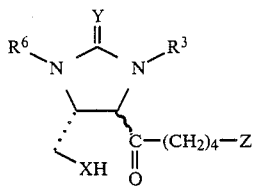

XV wherein $R^3$, $R^6$, X, Y and Z have the meaning given, this is cyclized, under the action of a base, to give a biotin derivative of the formula XVI

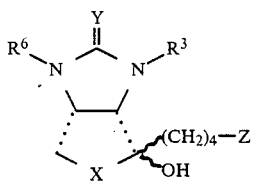

XVI wherein $R^3$, $R^6$, X, Y and Z have the meaning given, and this is converted into D-(+)-biotin by known processes, or by a procedure in which (c) XI is reacted with a reducing agent to give an aldehyde of the formula XVII

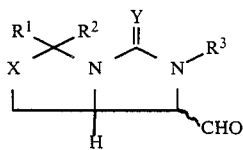

XVII wherein $R^1$, $R^2$, $R^3$, X and Y have the meaning given, this is condensed with an organophosphorus compound to give an unsaturated carboxylic acid of the formula XVIII

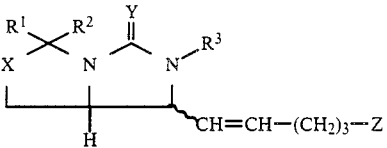

XVIII wherein $R^1$, $R^2$, $R^3$, X, Y and Z have the meaning given, this is converted by an acid and/or a reducing agent into a biotin derivative of the formula XIX

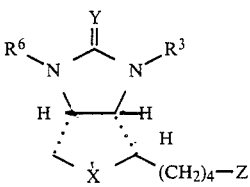

XIX wherein $R^3$, $R^6$, X, Y and Z have the meaning given, and this is converted into D-(+)-biotin by known processes, or by a procedure in which (d) an oxo compound of formula XIV given above is converted, under the action of an acid, to a biotin derivative of the formula XX

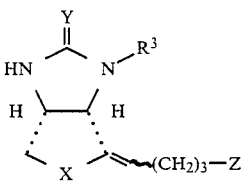

XX wherein $R^3$, X, Y and Z have the meaning given, and this is converted into D-(+)-biotin by known processes.

Furthermore the invention relates to compounds of the formula XI because these are useful intermediate products or starting materials opening of possibilities to synthesize optically active D-(+)-biotin.

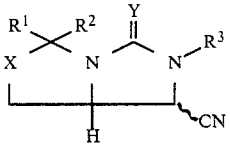

XI wherein $R^1$, $R^2$, X and Y have the meaning given and $R^3$ is a protective group which is suitable for a nitrogen atom. In this formula X is preferably S and Y is preferably O. Particularly preferred is the compound of the formula XIa, wherein $R^1$ is H, $R^2$ is phenyl and $R^3$ is benzyl.

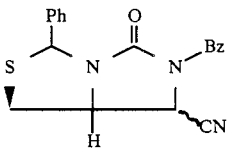

XIa

The compounds of the formula I are prepared by methods which are known per se, such as are described in the Literature (for example in standard works such as Houben-Weyl, Methoden der Organischen Chemie (Methods of Organic Chemistry), Georg-Thieme-Verlag, Stuttgart), and in particular under reaction conditions such as are known and suitable for the reactions mentioned. It is also possible for variants which are known per se and are not mentioned in more detail here to be utilized.

The starting substances of the formula II are known or can be prepared from L-cysteine or L-serine by known methods, such as are described, for example, in Schoberl, Hamm, Chem. Ber. 81 [1948], 210 and Karabinos, Szabo, J. Amer. Chem. Soc. 66 [1944], 649, by reacting the free amino acids or acid addition salts thereof with an alkali metal cyanate or thiocyanate or alkaline earth metal cyanate or thiocyanate with one another in a suitable solvent, such as water, alcohols or mixtures thereof, preferably at elevated temperature, and cyclizing the resulting intermediate product in situ, under the action of an acid, for example a mineral acid.

The reaction of the hydantoins of the formula II with carbonyl compounds of the formula III to give the bicyclic compounds of the formula IV can be carried out by the known customary methods for acetalizations, such as are described, for example, in Houben-Weyl, Methoden der Organischen Chemie (Methods of Organic Chemistry), volume VI/3, page 199. The reaction components are preferably reacted with the addition of a dehydrating agent, such as, for example, an acid, such as sulfuric acid, phosphoric acid, hydrochloric acid or p-toluenesulfonic acid, an acid derivative, such as phosphorus pentoxide, phosphorus trichloride, phosphorus pentachloride or phosphorus oxychloride, a metal salt, such as anhydrous calcium chloride, copper sulfate or iron(III) chloride, an acid ion, exchanger or molecular sieves. The water of reaction formed can also be removed by azeotropic distillation with a suitable solvent, such as benzene, toluene, chloroform or methylene chloride. Finally, it is also possible to use, instead of a free carbonyl compound of the formula III, the acetal thereof with a suitable alcohol, preferably a lower alcohol, for the preparation of the compounds of the formula IV. The alcohol liberated during the reaction is advantageously removed continuously from the reaction mixture, for example by distillation or adsorpion. Water of reaction formed by an excess of the acetal of the oxo compound III can also be removed.

One equivalent of carbonyl compound III or acetal thereof, which can simultaneously serve as the solvent, is advantageously used for the reaction with the hydantoins of the formula II. However, it is more advantageous to add an additional inert solvent. Preferred suitable inert solvents are hydrocarbons, such as pentane, hexane, cyclohexane, benzene, toluene or xylene, and chlorinated hydrocarbons, such as methylene chloride, chloroform or carbon tetrachloride.

The nitrogen atom in the bicyclic compounds of the formulae I, VIII, IX, X, XI, XII, XIII, XIV, XV, XVI, XVII, XVIII, XIX, and XX is protected by a protecting group $R^3$, wherein $R^3$ is e.g. benzyl, 4-methoxybenzyl, 3,4-dimethoxybenzyl, 4-methylbenzyl, allyl, methallyl, crotyl, methoxymethyl, trimethylsilyl, tert.-butyldimethylsilyl, or tert.-butyldiphenylsilyl. These protecting groups are introduced by known processes such as are to be found, for example in Mac Omie, Protective Groups in Organic Chemistry, Plenum Press, New York, 1973 by reacting the corresponding reactive halogen compounds with bicyclic compounds of the formula IV leading to (7R)-1H,3H-imidazo[1,5-c]-azoles of the formula I. The reaction partners are preferably reacted in a suitable solvent with the addition of a basic reagent. Especially suitable solvents are, in particular, ethers, such as diethyl ether, di-n-butyl ether, tetrahydrofuran, dioxane or anisole, ketones, such as acetone, butanone or cyclohexanone, amides, such as dimethylformamide or phosphoric acid hexamethyltriamide, hydrocarbons, such as benzene, toluene or xylene, halogenohydrocarbons, such as carbon tetrachloride or tetrachloroethylene, and sulfoxides, such as dimethylsulfoxide or sulfolane.

A prefered reaction procedure is the reaction of a bicyclic compound of the formula IV with a reactive compound which carries the radical $R^3$, preferably in a basic medium, bases which are of importance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, alkali metal hydrides, such as sodium hydride, amides, such as sodium amide or lithium diisopropylamide, alcoholates, such as sodium methylate, sodium ethylate or lithium ethylate, or organic bases, such as triethylamine, pyridine, lutidine, collidine, imidazole, 4-(N,N-dimethylamino)-pyridine or quinoline.

The reaction temperature is usually between $-50°$ C. and $+250°$ C., preferably between $-20°$ C. and $+80°$ C. At these temperatures, the reactions are as a rule ended after 15 minutes to 48 hours.

In another process for the preparation of the compounds of the formula II, L-cysteine or L-serine is reacted with a carbonyl compound of the formula III to give an azolidine V. Compounds of the formula V and processes for their preparation are known, for example, from Schubert, J. Biol. Chem. 114 (1936), 341, Uskovic et al., J. Amer. Chem. Soc. 97 (1975), 5936, Lieberman et al., ibid. 70 (1948), 3094 and U.S. Pat. No. 3,957,794 and U.S. Pat. No. 4,009,172. The reaction conditions described for the preparation of the compounds of the formula IV are also suitable.

Azolidines of the formula V can be converted into compounds of the formula IV by means of alkali metal cyanates or thiocyanates or alkaline earth metal cyanates or thiocyanates under the reaction condtions already described for the preparation of compounds of the formula II, and these can be further converted into the imidazo[1,5-c]-azoles of the formula I as described.

However, it is more advantageous for the azoles of the formula V to be reacted with an organo-isocyanate or -isothiocyanate of the formula VI directly to give the imidazo[1,5-c]azoles of the formula I. Organo-isocyanates and -isothiocyanates of the formula VI are known or can be obtained by known methods, such as are described, for example, in Houben-Weyl, Methoden der Organischen Chemie (Methods of Organic Chemistry), volumes VIII, page 75 and IX, page 773.

The reaction of hydantoins with phenyl isocyanate and methyl isocyanate is known from Lieberman, J. Amer. Chem. Soc. 70 (1948), 3094 and Crabb et al., Tetrahedron 29 (1973), 3389. The reaction of the azoles of the formula V with the organoisocyanates or -isothiocyanates of the formula VI can also be carried out by these methods. The reaction components are preferably reacted in a suitable-solvent, such as, for example, ethers, such as diethyl ether, di-n-butyl ether, tetrahydrofuran, dioxane or anisole, ketones, such as acetone, butanone or cyclohexanone, amides, such as dimethylformamide or phosphoric acid hexamethyltriamide, hydrocarbons, such such as benzene, toluene or xylene, halogenohydrocarbons, such as carbon tetrachloride or tetrachloroethylene, and sulfoxides, such as dimethylsulfoxide or sulfolane. Basic solvents, such as pyridine, lutidine, collidine, diethylamine or triethylamine, and mixtures of these bases with the abovementioned solvents are also suitable.

If appropriate, it may be advantageous for the carbamoyl or thiocarbamoyl compound primarily formed to be isolated and cyclized in a separate reaction step, water being split off. Examples of suitable dehydrating agents are acids, such as sulfuric acid, hydrogen chloride or toluene sulfonic acid, or bases, such as sodium hydroxide or potassium hydroxide. The reaction here can be carried out in the presence or absence of an inert solvent at temperatures between about 0° C. and 150° C., preferably between about 20° C. and 100° C.; examples of possible solvents are water and alcohols, such as methanol, ethanol, isopropanol or butanol.

In another process for the preparation of the compounds of the formula II, L-cystine is reacted with an alkali metal cyanate or thiocyanate or alkaline earth metal cyanate or thiocyanate to give a bis-hydantoin of the formula VII. The same methods which have already been described for the preparation of the hydantoins of the formula II can be used for this, the same or similar reaction conditions being applied.

Hydantoins of the formula II ($X=S$) can be obtained from the bis-hydantoins of the formula VII by treatment with a reducing agent, and the imidazo[1,5-c]thiazoles of the formula I ($X=S$) can be prepared from these by the methods described above. Suitable reducing agents are to be found, for example, in Houben-Weyl, Methoden der Organischen Chemie (Methods of Organic Chemistry), volume 15/1, page 798. Sodium/liquid ammonia, zinc/acid or phosphonium iodide are preferably suitable for reductive cleavage of the disulfide bond. The reduction of the bis-hydantoins of the formula VII is preferably carried out with one equivalent, or in particular with an excess, of reducing agent in a suitable solvent adapted to the chemical nature of the reagent, such as, for example, water, liquid ammonia, alcohols, such as methanol, ethanol or isopropanol, acids, such as hydrochloric acid, sulfuric acid, formic acid or acetic acid, ethers, such as diethyl ether, tetrahydrofuran or dioxane, or mixtures thereof, advantageously at temperatures between about $-50°$ C. and $+150°$ C.

A particularly advantageous process for cleavage of the disulfide bond in the compounds of the formula VII comprises thiolysis thereof with a suitable mercaptan, such as, for example, thiophenol, butane-1,4-dithiol or 1,4-dithio-threitol, by a procedure analogous to that described by Hase and Walter, Inst. J. Pept. Prot. Res. 5 (1973), 283. The reaction components are advantageously reacted in a suitable solvent, such as, for example, aqueous alkali metal hydroxide solutions, chlorohydrocarbons or liquid ammonia, at temperatures between about $-40°$ C. and $+120°$ C.

The bis-hydantoins of the formula VII can furthermore be provided with a protective group of the formula $R^3$. The methods already described for the preparation of the compounds of the formula I from the bicyclic compounds of the formula IV can be used for the preparation of these protected bis-hydantoins of the formula VIII, the same or similar reaction conditions being applied.

Another process for the preparation of the protected bis-hydantoins of the formula VIII comprises reaction of L-cystine with an organo-isocyanate or -isothiocyanate of the formula VI mentioned by a process analogous to the preparation of compounds of the formula I from azolidines of the formula V, the same or similar processes as have already been described for the preparation of the compounds of the formula I being used.

For conversion of the compounds of the formula VIII into the (7aR)-1H,3H-imidazo[1,5-c]thiazoles of the formula I ($X=S$), these are treated with a reducing agent or a reagent which effects thiolysis in a manner corresponding to the preparation of the hydantoins of the formula II from the disulfides of the formula VII, the same or similar processes and reaction conditions being used, and the products are then reacted with a carbonyl compound of the formula III, in accordance with the preparation of compounds of the formula V.

One process for the preparation of D-(+)-biotin from I comprises reducing an oxo compound of the formula I to an alcohol of the formula IX. Suitable processes are to be found, for example, in Houben-Weyl, Methoden der Organischen Chemie (Methods of Organic Chemistry), volume 4/1c+4/1d.

The reduction can be carried out, for example, by catalytic hydrogenation at temperatures between about 0° C. and about 200° C. under pressures between about 1 and 200 bar in an inert solvent, for example an alcohol, such as methanol, ethanol, isopropanol, an ether, such as tetrahydrofuran (THF) or dioxane, an ester, such as ethyl acetate, a carboxylic acid, such as acetic acid, or a hydrocarbon, such as cyclohexane. Advantageously suitable catalysts are noble metals, such as Pt or Pd, which can be used in the form of oxides (for example $PtO_2$ or PdO) on a support (for example Pd on charcoal, calcium carbonate or strontium carbonate), or in finely divided form.

Reductions with complex hydrides, such as, for example, boranes, such as diborane, sodium boranate or lithium cyano-trihydro-borate, metal hydrides, such as sodium hydride or aluminium hydride, silicon hydrides, such as triethylsilane, tributyl-tin hydride and mixed hydrides, such as lithium alanate, sodium alanate or sodium bis-(2-methoxy-ethoxy)-dihydridoaluminate, or potassium boranate or lithium boranate, are furthermore possible.

The reaction of the oxo compounds of the formula I with the reducing agents is advantageously carried out in a suitable solvent at temperatures between about $-100°$ C. and $+150°$, in particular between about 0° and 100°; examples of possible solvents are water, alcohols, such as methanol, ethanol, isopropanol or butanol, ethers, such as tetrahydrofuran, dioxane, diethyl ether or ethylene glycol dimethyl ether, and hydrocarbons, such as pentane, cyclohexane, benzene and toluene, depending on the chemical nature of the reducing agent.

For activation of the hydroxyl group in the alcohols of the formula IX, these are reacted with a reactive compound $R^4$—Q carrying the radical $R^4$, wherein $R^4$ is, for example, alkanoyl, such as acetyl, aroyl, such as benzoyl or 4-nitrobenzoyl, alkylsulfonyl, such as methanesulfonyl, ethanesulfonyl or trifluoromethanesulfonyl, arylsulfonyl, such as phenylsulfonyl, or aralkylsulfonyl, such as benzylsulfonyl. $R^4$ is furthermore a radical azole-M, wherein azole is a nitrogen-containing, unsubstituted or substituted and/or fused, five-membered ring, such as, for example, imidazole, 1,2,4- triazole, 1,2,3-triazole, benzotriazole, benzimidazole, pyrazole, 3,5-dimethylpyrazole or indazole, and M is CO, CS, SO, SO$_2$ or S. Preferably, R$^4$ is acetyl, imidazole-1-ylcarbonyl, imidazole-1-ylsulfinyl imidazole-1-ylsulfonyl. Q is halogen, alkoxy, alkanoyloxy or a further azole radical. Suitable groups for R$^4$ and Q are those corresponding groups defined above for R$^1$-R$^2$. Accordingly, the reaction of acetyl chloride, acetic anhydride, 1,1'-carbonyldiimidazole, 1,1'-sulfinyldiimidazole and 1,1'-sulfonyldiimidazole with alcohols of the formula IX is particularly suitable for the preparation of active esters of the formula X.

A preferred reaction procedure is the reaction of an alcohol of the formula IX with a reactive compound which carries the radical R$^4$, preferably in a basic medium, particularly suitable bases being organic bases, such as triethylamine, pyridine, lutidine, collidine or quinoline. The reaction temperature is usually between $-50°$ C. and $+150°$ C., preferably between $-20°$ C. and $+80°$ C. At these temperatures, the reactions are as a rule ended after 15 minutes to 48 hours.

For conversion into nitriles of the formula XI, the activated esters of the formula X can be reacted with a cyanide, advantageously with a metal cyanide, such as sodium cyanide, potassium cyanide or copper cyanide or cyanosilane, such as, for example, trimethylsilyl cyanide, β-trimethylsilypropionitrile or diethylaluminium cyanide, for example, in an inert solvent, such as methylene chloride, toluene, pyridine, dimethylformamide, dimethylsulfoxide, N-methylpyrrolidone or hexamethylphosphoric acid triamide, at temperatures between $-50°$ C. and 200° C.

A preferred process for the preparation of nitriles of the formula XI from activated esters of the formula x wherein R$^4$ is a radical azole-M with the abovementioned meaning comprises additional activation of the esters of the formula X by N-alkylation thereof. Examples of alkylating agents which are suitable for this are alkyl, alkenyl and aryl iodides, bromides, chlorides, sulfates and sulfonates. Reaction thereof with the activated esters of the formula X is advantageously carried out in a suitable solvent, such as, for example, ethers, such as diethyl ether, tetrahydrofuran or dioxane, or ketones, such as acetone, diethyl ketone or methyl isobutyl ketones; however, the reaction can also be carried out without the additional of a solvent.

A further preferred process for the preparation of nitriles of the formula XI from esters of the formula X comprises the reaction of the latter with a cyanosilane according to methods such as are to be found, for example, in M. T. Reetz et al., Tetrahedron 39 (1983) 961; T. Hiyama et al., Synthesis 1986 689 or Houben-Weyl, Volume E5, pages 1389 ff (1985).

Particularly suitable compounds for this reaction are those compounds of the formula X wherein R$^4$ is alkanoyl or aroyl, especially alkanoyl, such as acetyl. Trimethylisyl cyanide proves to be a particularly suitable cyanation reagent. Advantageously, the reactants are reacted with one another in an inert solvent, such as, for example, methylene chloride or toluene, at temperatures of $-50°$ C. to 150° C., if appropriate with addition of a catalyst such as, for example, tin(IV) chloride, titanium(IV) chloride, tin(IV) triflate or zinc bromide.

The esters of the formula X can be isolated and be reacted with a cyanide in the abovementioned manner to give the nitriles of the formula XI, but they can also be formed in situ and reacted with a cyanide without being isolated.

Nitriles of the formula XI can be reacted with bases or acids to give acids of the formula XII in which R$^5$ is H, particularly suitable bases being alkali metal hydroxides, such as sodium hydroxide or potassium hydroxide, alkali metal carbonates or bicarbonates, such as sodium carbonate, sodium bicarbonate, potassium carbonates or potassium bicarbonate, or alkaline earth metal hydroxides, such as calcium hydroxide. Examples of suitable acids are hydrochloric acid, sulfuric acid or hydrobromic acid. The reaction temperature is usually between $-20°$ C. and $+200°$ C., preferably between 0° C. and $+100°$ C. At these temperatures, the reactions are as a rule ended after between 30 minutes and 48 hours.

Nitriles of the formula XI can be reacted with alcohols R$^5$—OH under acid catalysis to give acid derivatives of the formula XII in which R$^5$ is lower alkyl, cycloalkyl or aryl. Suitable acides are, in particular, hydrogen chloride, sulfuric acid and boron trifluoride, for example in the form of its diethyl ether adduct. The reaction is advantageously carried out in an excess of the alchol R$^5$—OH as the solvent, at temperatures between 0° C. and $+150°$ C.

The known lactones of the formula XIII can be obtained from the acid derivatives of the formula XII by liberating the hydroxymethyl (X=O) or mercaptomethyl (X=S) group again from the former and cyclizing the intermediate products thus obtained, of the formula XIIa,

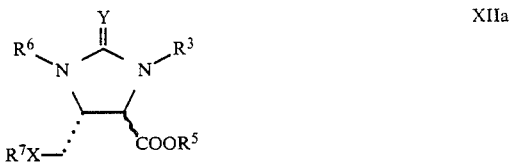

wherein X, Y, R$^3$ and R$^5$ have the abovementioned meaning, R$^6$ is H or CHR$^1$R$^2$ and R$^7$ is H, alkanoyl or aroyl, water (R$^5$=H) or alchol (R$^5$≠H) being split off.

Acids, such as hydrochloric acid or sulfuric acid, for example, are suitable for cleavage of the bicyclic compounds of the formula XII and lead to the hydantoins of the formula XIIa wherein R$^6$=R$^7$=H, advantageously in a solvent, for example water or alcohols.

Cleavage reagents which can furthermore be used are heavy metal salts, such as silver nitrate, mercury(II) chloride or mercury(II) acetate, and the metal mercaptides intermediately formed are subsequently decomposed with hydrogen sulfide. Examples of suitable solvents for this cleavage reaction are, after the alcohols, such as methanol or ethanol, amides, such as dimethylformamide, or ethers, such as tetrahydrofuran.

Acid derivatives of the formula XII in which X is S can be converted with reducing agents into intermediate products of the formula XIIa wherein R$^6$ is CHR$^1$R$^2$ and X is SH. Examples of suitable reducing agents are metals, such as zinc. The cleavage of the acid derivatives by reduction with metals is preferably carried out in an acid medium. Examples of suitable acids for this are mineral acids, such as hydrochloric acid or sulfuric acid, or organic acids, such as formic acid or acetic acid. These acids are advantageously used as solvents or as a mixture with other solvents, such as, for example, alcohols. The reaction temperature is usually between 0° C. and 200° C., preferably between 20° C. and 150° C. At these temperatures, the reactions are as a rule ended after between 15 minutes and 24 hours.

Under the conditions described above, compounds of the formula XIIa, wherein $R^7$ is H, are usually obtained. If, however, the reduction is carried out in an anhydrous medium with addition of an acylating agent, such as, for example, an acid halide or acid anhydride, compounds of the formula XIIa, in which $R^7$ is alkanoyl or aroyl, are obtained. Such compounds are preferentially suitable for conversion to lactones of the formula XIII.

The resulting intermediate products of the formula XIIa can be isolated; however, they are advantageously further reacted in situ to give the known lactones of the formula XIII. The latter lactones are frequently already formed to a high degree or already completely formed during cleavage of the bicyclic compounds of the formula XII. To form the lactones of the formula XIII from the intermediate products of the formula XIIIa, these are treated with an agent which effects the removal of water or alcohol. Examples of suitable agents which are available for this are alkali metal salts, such as potassium acetate or sodium acetate, acids, such as methanesulfonic acid, p-toluenesulfonic acid, phosphoric acid, sulfuric acid or hydrochloric acid, anhydrides, such as acetic anhydride or trifluoroacetic anhydride, or other dehydrating reagents, such as, for example, aluminium oxide, potassium hydroxide, cyanic acid or dicyclohexylacarbodiimide. The use of an excess of the abovementioned lactonizing agent frequently proves to be advantageous. Suitable reaction conditions for the lactonization can be found, for example, in Houben-Weyl, Methoden der Organischen Chemie (Methods of Organic Chemistry), volume E5.

Compounds of the formula XIIa, wherein $R^7$ is alkanoyl or aroyl, can advantageously be converted to lactones of the formula XIII, by subjecting their corresponding alkali metal salts, especially their sodium or potassium salts (XIIa, $R^5$=Na or K) to a thermal epimerization/cyclization. The reaction of the alkali metal salts of carboxylic acids of the formula XII, which salts may have been prepared in situ, is advantageously carried out in an inert solvent such as dimethylformamide, dimethylacetamide, dimethylsulfoxide or N-methylpyrrolidone, at temperatures of 30°-200° C., especially at 50°-150° C. The reaction times are from 30 minutes to 12 hours.

The conversion of the lactones of the formula XIII into D-(+)-biotin is known, for example, from German Patent 2,058,234 and German Patent 2,331,244.

In another process for the preparation of D-(+)-biotin from (7aR)-1H,3H-imidazo[1,5-c]azoles of the formula I, nitriles of the formula XI are reacted with and organometallic compound to give oxo compounds of the formula XIV. Organometallic compounds which are suitable for this are, for example, those of magnesium (Blaise process), of zinc (Reformatzky process), fo lithium or of aluminium. The reaction conditions for the reaction of the organometallic compounds depend on the nature and chemical reactivity of the functional groups present and can be chosen analogously to known processes, such as are described, for example, in Houben-Weyl, Methoden der Organischen Chemie (Methods of Organic Chemistry), volume VII/2a, page 603.

The same abovementioned methods for the preparation of the hydantoins of the formula XIIa from the acid derivatives XII are suitable for conversion of the bicyclic oxo compounds of the formula XIV into the hydantoins of the formula XV by means of an acid or a reducing agent. On cleavage by means of acids, imidazolidines of the formula XV in which $R^6$ is H are obtained, and on cleavage by a reducing agent, $R^6$ in formula XV is $R^1R^2CH$. The reaction conditions correspond to the abovementioned methods.

Compounds of the formula XV can be cyclized under basic conditions to give the hemiacetals of the formula XVI. Examples of bases which are suitable for this are alkali metal hydroxides, such as sodium hydroxide or potassium hydroxide, alkali metal carbonates, such as sodium bicarbonate, potassium carbonate or potassium bicarbonate, alkali metal acetates, such as sodium acetate or potassium acetate, alkaline earth metal hydroxides and oxides, such as calcium hydroxide, calcium oxide or aluminium oxide, or organic bases, such as triethylamine, pyridine, lutidine, piperidine, morpholine, piperazine, collidine or quinoline. Basic ion exchangers are furthermore also suitable for cyclization of compounds of the formula XV. The reaction is advantageously carried out in an inert solvent. Suitable preferred inert solvents are hydrocarbons, such as cyclohexane, benzene and toluene, ethers, such as tetrahydrofuran and dioxane, amides, such as dimethylformamide and hexamethylphosphoric acid triamide, sulfoxides, such as dimethylsulfoxide, alcohols, such as methanol and ethanol, esters, such as ethyl acetate, or lower carboxylic acids, such as formic acid or acetic acid. An excess of organic base is also suitable as the solvent, and in combination with a lower carboxylic acid is a particularly preferred cyclization medium. The reaction temperatures are advantageously between about 0° and 200°, preferably between 20° and 150°, and the reaction times are between 1 and 48 hours.

Hemiacetals of the formula XVI are known and can be converted into D-(+)-biotin by known methods, such as are to be found, for example, in German Patent 2,058,234.

In another process for the preparation of D-(+)-biotin from (7aR)-1H,3H-imidazo[1,5-c]azoles of the formula I, nitriles of the formula XI are reacted with a reducing agent to give an aldehyde of the formula XVII. Processes which are suitable for this are to be found, for example, in Houben-Weyl, Methoden der Organischen Chemie (Methods of Organic Chemistry), volumes 7/1, page 299 and E3, page 476. Examples of reducing agents which can be used are tin(II) chloride with hydrogen chloride in ethereal solution or hydrogen under Raney nickel catalysis in an acid medium. Good results can also be achieved by reaction of the nitriles of the formula XI with 2-mercaptoethanol to give the corresponding 2-substituted 1,3-benzooxathia -zoles and reduction thereof by means of sodium borohydride. The reduction of the nitriles of the formula XI is particularly advantageously carried out with complex hydrides, such as sodium hydro-triethoxyaluminate, lithium hydro-triethoxyalanate or, particularly preferably, with diisobutylaluminum hydride.

The reaction of the complex hydrides with the nitriles of the formula XI is advantageously carried out in an inert solvent. Preferred suitable inert solvents are hydrocarbons, such a spentane, hexane, cyclohexane, benzene or toluene, or ethers, such as diethyl ether, tetrahydrofuran, dioxane or ethylene glycol dimethyl ether, and mixtures of these solvents with one another. The reaction temperatures are advantageously between about −120° C. and +150° C., preferably between −80° C. and +100° C., and the reaction times are between about 30 minutes and 24 hours.

The unsaturated compounds of the formula XVIII can be prepared from the aldehydes of the formula XVII with suitable phosphorus-organyls in the presence of a base. Thus, for example, phosphoranes, after conversion into the corresponding ylides by the processes described in Houben-Weyl, Methoden der Organischen Chemie (Methods of Organic Chemistry), volume 5/16, page 383, phosphonates, after formation of the anion analogously to the processes descibed, for example, in Organic Reactions, volume 25, John Wiley, New York, 1978, Chapter 2, or phosphine oxides can be used for the olefination of aldehydes of the formula XVII in the manner described, for example, in Houben-Weyl, Methoden der Organischen Chemie (Methods of Organic Chemistry), volume XII/1, page 167. Suitable bases for preparation of a reactive phosphorylide, phosphonate or phosphine oxide anion, depending on the ease of deprotoation of the phosphorus-organyl employed, are, for example, alkali metal hydroxides, such as sodium hydroxide or potassium hydroxide, alkali metal carbonates, such as sodium carbonate or potassium cabonate, alcoholates, such as sodium methylate, sodium ethylate, lithium ethylate or potassium tert.-butanolate, alkali metal amides, such as potassium amide or sodium amide, alkali metal-organyls, such as methylithium, butyllithium or phenyllithium, or other orgainc bases, such as lithium diisopropylamide or sodium methylsulfinylmethylide. The reaction is advantageously carried out in an inert solvent. Preferred suitable inert solvents are ethers, such as diethyl ether, ethylene glycol dimethyl ether, tetrahydrofuran or dioxane, and amides, such as dimethylformamide, hexamethylphosphoric acid triamide, dimethylacetamide or N-methylpyrrolidone, and furthermore sulfoxides, such as dimethylsulfoxide or sulfolane, as well as hydrocarbons, such as pentane, hexane, cyclohexane, benzene or toluene. The reaction temperatures are advantageously between about $-10°$ C. and about $+150°$ C., preferably between $+20°$ C. and $+100°$ C., depending on the reactivity of the phosphorus-organyl employed, and the reaction times are between 1 and 48 hours.

The unsaturated bicyclic compounds of the formula XVIII are reacted with acids and/or reducing agents by processes which are analogous to those described above for cleavage of acid derivatives of the formula XII. Hydroxy-(X=O) or mercapto-(X=S)-methyldantonins formed as intermediate products undergo cyclization under the cleavage conditions to give the biotin derivatives of the formula XIX, $R^6$ being H in the case of acid cleavage; in the case of cleavage by a reducing agent, $R^6$ is $R^1R^2CH$. The reaction conditions correspond to the methods described above.

Finally, oxo compounds of the formula XIV can be converted, by processes described above, which are analogous to the cleavage of acid derivatives of the formula XII, to give biotin derivatives of the formula XX, where $R^3$, X, Y and Z have the meaning given.

Biotin derivatives of the formula XIX are known and can be converted into D-(+)-biotin by known methods, such as are disclosed, for example, in German Patent 2,058,234, European Patent 0,036,030 and European Patent 0,084,377.

The process according to the invention thus enables optically active D-(+)-biotin to be prepared in a simple stereo specific manner in high yields from readily accessible cheap starting substances in a few synthesis steps, some of which can be carried out in a one-pot process, and thus represents a substantial advance in the field of biotin synthesis.

All starting material are known or readily preparably from known starting materials using fully conventional methods.

The full disclosure of any references and applications mentioned above and below are hereby incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages ar by weight; unless otherwise indicated.

EXAMPLE 1

6.53 g (0.3 mol) of lithium borohydride are added in portions to a solution of 97.32 g (0.3 mol) of (7aR)-3-phenyl-6-benzyl-1H,3H-imidazol[1,5-c]thiazole-5,7(6H,7aH)-dione in 800 ml of tetrahydrofuran, kept under nitrogen, at $+5°$ C. and the mixture is then stirred at room temperature for 3 hours.

It is then carefully decomposed with 400 ml of ice-water, most of the tetrahydrofuran is distilled off and the product is extracted with a total of 800 ml of ethyl acetate.

The organic phases are combined, washed twice with 150 ml of water each time, dried over sodium sulfate and concentrated under reduced pressure.

90.8 g (7RS,7aR)-3-phenyl-6-benzyl-7,7a-dihydro-7-hydroxy-1H,3H-imidazol[1,5-c]thiazol-5-(6H)-one with a melting point of $151°-153°$ C. are obtained.

$[\alpha]_{365}^{20} = -875°$, c=1 (methanol).

EXAMPLE 2

A solution of 43.35 g (1.1 mol) of 96% sodium borohydride in 300 ml of water is allowed to run, at room temperature, into a solution of 324.4 g (1 ml) of (7aR)-3-phenyl-6-benzyl-1H,3H-imidazol[1,5-c]thiazole-5,7(6H,7aH)-dione in 1200 ml of tetrahydrofuran and the reaction mixture is stirred for 12 hours at 50° C. It is then cooled to 20° C., the aqueous phase is separated off and the organic solution is concentrated under reduced pressure.

The residue is suspended in 1000 ml of 2-propanol, 100 ml of solvent are distilled off and the mixture is left to crystallize at 0° C.

303.5 g of (7R,7aR)-3-phenyl-6-benzyl-7,7a-dihydro-7-hydroxy-1H,3H-imidazo[1,5-c]thiazole-5(6H)-one, with a melting point of $174°-175°$ C., are obtained.

$[\alpha]_{365}^{20} = -1026°$, c=1 (methanol).

EXAMPLE 3

A solution of 43.35 g (1.1 mol) of 96% sodium borohydride in 300 ml of water is allowed to run into a solution of 324.4 g (1 mol) of (7aR)-3-phenyl-6-benzyl-1H,3H-imidazo[1,5-c]thiazooe-5,7(6H,7aH)-dione in 1200 ml of tetrahydrofuran at room temperature and the reaction mixture is stirred for 7 hours at 50° C. It is then cooled to 20° C., the aqueous phase is separated off and the organic solution is concentrated under reduced pressure.

The residue is suspended in 1000 ml of 2-propanol, 100 ml of solvent are distilled off and the residue is left to crystallize at 0° C.

298.7 g of (7RS,7aR)-3-phenyl-6-benzyl-7,7a-dihydro-7-hydroxy-1H,3H-imidazo[1,5-c]thiazole-5(6H)-one, with a melting point of 164°–166° C., are obtained.

$[\alpha]_{365}^{20} = -964°$, c=1 (methanol).

EXAMPLE 4

50.27 g (0.31 mol) of 1,1-carbonyldiimidazole are introduced at +10° C. into a suspension of 97.92 g (0.3 mol) of (7RS,7aR)-3-phenyl-6-benzyl-7,7a-dihydro-7-hydroxy-1H,3H-imidazo[1,5-c]thiazol-5(6H)-one in 300 ml of acetonitrile, kept under nitrogen, in the course of 30 minutes. The resulting clear solution is stirred at room temperature for 30 minutes and concentrated and the residue is partitioned between 300 ml of water and 500 ml of ethyl acetate. The organic phase is washed three times with 100 ml of water each time, dried over sodium sulfate and concentrated under reduced pressure.

104.6 g of (7RS,7aR)-3-phenyl-6-benzyl-7,7a-dihydro-7-(imidazol-1-ylcarbonyloxy)-1H,3H-imidazo[1,5-c]thiazol-5(6H)-one are obtained as an oil.

$[\alpha]_{365}^{20} = -750°$, c=1 (methanol).

EXAMPLE 5

A solution of 9.79 g (30 mmol) of (7RS,7aR)-3-phenyl-6-benzyl-7,7a-dihydro-7-hydroxy-1H,3H-imidazo[1,5-c]thiazol-5(6H)-one in 100 ml of tetrahydrofuran is added dropwise to a suspension of 0.96 g (32 mmol) of 80% pure sodium hydride in 20 ml of tetrahydrofuran at room temperature under nitrogen and the solution formed is stirred at room temperature for 45 minutes. A solution of 6.34 g (32 mmol) of 1,1-sulfonyldiimidazole in 80 ml of tetrahydrofuran is then added dropwise at room temperature in the course of 10 minutes and the mixture is stirred for a further 20 minutes.

The mixture is concentrated, 200 ml of ice-water are added to the residue and the mixture is extracted three times with 100 ml of diethyl ether each time. The combined organic phases are dried over sodium sulfate and concentrated under reduced pressure.

Chromatography of the residue on silica gel (ethyl acetate) gives 8.1 g of (7RS,7aR)-3-phenyl-6-benzyl-7,7a-dihydro-7-(imidazol-1-ylsulfonyloxy)-1H,3H-imidazo[1,5-c]thiazol-5(6H)-one as an oil.

$[\alpha]_{365}^{20} = -710°$, c=1 (methanol).

EXAMPLE 6

33.69 g (0.33 mol) of acetic anyhdride are added dropwise, over 10 minutes, to a solution of 97.92 g (0.3 mol) of (7RS,7aR)-3-phenyl-6-benzyl-7,7a-dihydro-7-hydroxy-1H,3H-imidazo[1,5-c]thiazol-5(6H)-one in 900 ml of pyridine and the solution is stirred for 12 hours at room temperature. It is then concentrated under reduced pressure, the residue is dissolved in 600 ml of toluene, the solution is washed three times with 100 ml of 1N hydrochloric acid at a time, and the solvent is distilled off.

110.1 g of (7RS,7aR)-3-phenyl-6-benzyl-7,7a-dihydro-7-acetoxy-1H,3H-imidazo[1,5-c]thiazol-5(6H)-one are obtained as an oil.

$[\alpha]_{365}^{20} = -786°$, c=1 (methanol).

EXAMPLE 7

354.85 g (2.5 mol) of iodomethane are added dropwise to a solution of 210.24 g (0.5 mol) of (7RS,7aR)-3-phenyl-6-benzyl-7,7a-dihydro-7-(imidazol-1-ylcarbonyloxy)-1H,3H-imidazo[1,5-c]thiazol-5(6H)-one in 1500 ml of acetone in the course of 10 minutes and the solution is stirred at room temperature for 3 hours.

It is then concentrated, the residue is dissolved in 750 ml of dimethylformamide, 98.02 g (2 mol) of sodium cyanide are added and the mixture is stirred at 75° C. for one hour.

The solution is then stirred into 5000 ml of ice-water and the mixture is extracted five times with 500 ml of toluene each time. The combined organic phases are washed with water and saturated sodium chloride solution, dried over sodium sulfate and concentrated under reduced pressure.

150.7 g of a mixture of (7R,7aR)- and (7S,7aR)-3-phenyl-6-benzyl-7cyano-7,7a-dihydro-1H,3H-imidazo[1,5-c]thiazol-5(6H)-one are obtained as an oil, which is chromatographed on silica gel with petroleum ether/tert.-buty methyl ether (1:1, volume/volume).

7S-Nitrile: Yield 35 g; melting point: 102°–103° C.
$[\alpha]_{365}^{20} = -795°$, c=1 (methanol).

7R-Nitrile: Yield 107 g: melting point: 109°–110° C.
$[\alpha]_{365}^{20} = -840°$, c=1 (methanol).

EXAMPLE 8

45.65 g (0.1 mol) of (7RS,7aR)-3-phenyl-6-benzyl-7,7a-dihydro-7-(imidazol-1-sulfonyloxy)-1H,3H-imidazo[1,5-c]-thiazol-5(6H)-one are taken in 350 ml of acetone. 60.49 g (0.5 mol) of allyl bromide are added dropwise to this solution in the course of 5 minutes and the reaction mixture is stirred at room temperature for 30 minutes.

The mixture is then concentrated, the residue is dissolved in 100 ml of 1-methyl-2-pyrrolidone, 19.6 g (0.4 mol) of sodium cyanide are added to the solution and the mixture is stirred at 80° C. for 45 minutes.

The reaction mixture is then stirred into 1000 ml of ice-water and extracted three times with 200 ml of toluene each time. The combined organic phases are washed with water and saturated sodium chloride solution, dried over sodium sulfate and concentrated under reduced pressure. 16.8 g of a mixture of (7R,7aR)- and (7S,7aR)-3-phenyl-6-benzyl-7-cyano -7,7a-dihydro-1H,3H-imidazo[1,5-c]thiazol-5(6H)-one are obtained as an oil, which is chromatographed on silica gel with petroleum ether/tert.-butyl methyl ether (1:1, volume/volume).

7S-Nitrile: yield 3.8 g; melting point: 103° C.
$[\alpha]_{365}^{20} = -790°$.

7R-Nitrile: yield 11.8 g; melting point: 109°–110° C.
$[\alpha]_{365}^{20} = -845°$. c=1 (methanol).

EXAMPLE 9

104.17 g (1.05 mol) of trimethylsily cyanide are run at −20° C. into a solution, kept under nitrogen, of 368.45 g (1 mol) of (7RS,7aR)-3-phenyl-6-benzyl-7,71-dihydro-7-acetoxy-1H,3H-imidazo[1,5-c]thiazol-5(6H)-one in 3500 ml of methylene chloride, 189.71 g (1 mol) of titanium(IV) chloride are then added over 15 minutes, with vigorous stirring, the mixture is stirred for 45 minutes at −20° C.

1000 ml of 1 N hydrochloric acid are added cautiously to the red reaction mixture at 0° C. and the batch is stirred at room temperature until completely colourless.

The organic phase is then separated off, washed twice with 1000 ml of water at a time, dried over sodium sulphate and concentrated.

321.3 g of (7RS,7aR)-3-phenyl-6-benzyl-7-cyano-7,7a-dihydro-1H,3H-imidazo[1,5-c]thiazol-5-(6H)-one are obtained as an oil.

$[\alpha]_{365}^{20} = -823°$, c=1 (methanol).

EXAMPLE 10

31.64 g (0.4 mol) of pyridine and 33.69 g (0.33 mol) of acetic anhydride are added to a suspension of 97.92 g (0.3 mol) of (7RS,7aR)-3-phenyl-6-benzyl-7,7a-dihydro-7-hydroxy-1H,3H-imidazo[1,5-c]thiazol-5(6H)-one in 1200 ml of toluene and the mixture is stirred for 10 hours at 50° C.

The solution is cooled to room temperature and washed three times with 200 ml of 1 N hydrochloric acid at a time, and 200 ml of toluene are distilled off.

When the residue has cooled to −20° C., 30.76 g (0.31 mol) of trimethylsilyl cyanide are added under nitrogen, and 56.91 g (0.3 mol) of titanium(IV) chloride are introduced dropwise over 5 minutes.

350 ml of 1 N hydrochloric acid are cautiously added dropwise, at 0° C., to the brown reaction mixture, which is stirred at room temperature until completely colourless.

The organic phase is separated off, washed twice with 300 ml of water at a time and concentrated.

89.6 g (7RS,7aR)-3-phenyl-6-benzyl-7-cyano-7,7a-dihydro-1H,3H-imidazo[1,5-c]thiazol-5(6H)-one are obtained as an oil.

$[\alpha]_{365}^{20} = -817°$, c=1 (methanol).

EXAMPLE 11

47.46 g (0.6 mol) of pyridine and 33.69 g (0.33 mol) of acetic anhydride are added to a solution of 97.92 g (0.3 mol) of (7RS,7aR)-3-phenyl-6-benzyl-7,7a-dihydro-7hydroxy-1H,3H -imidazo[1,5-c]thiazol-5(6H)-one in 960 ml of methylene chloride and the mixture is boiled under reflux for 8 hours.

It is then cooled to room temperature, washed three times with 300 ml of 1N hydrochloric acid at a time and dried over sodium sulphate.

The solution is then cooled to −20° C., 30.76 g (0.31 mol) of trimethylsilyl cyanide are run in under nitrogen and 78.15 g (0.3 mol) of tin(IV) chloride are introduced dropwise over 5 minutes. 350 ml of 1N hydrochloric acid are then added cautiously to the reaction mixture at 0° C. and the mixture is stirred at room temperature until completely colourless.

The organic phase is separated off, washed twice with 300 ml of water at a time and dried over sodium sulphate and concentrated.

86.3 g of (7RS,7aR)-3-phenyl-6-benzyl-7-cyano-7,7a-dihydro-1H,3H-imidazo[1,5-c]thiazol-5(6H)-one are obtained as oil.

]$\alpha]_{365}^{20} = -826°$, c=1 (methanol).

Analogously are obtained:
(7RS,7aR)-3-phenyl-6-(4-methoxybenzyl)-7-cyano-7,7a-dihydro-1H,3H -imidazo[1,5c]thiazo-5(6H)-one
(7RS,7aR)-3-phenyl-6-(4-chlorbenzyl)-7-cyano-7,7a-dihydro-1H,3H -imidazo[1,5c]thiazo-5(6H)-one
(7RS,7aR)-3-phenyl-6-(4-nitrobenzyl)-7-cyano-7,7a-dihydro-1H,3H -imidazo[1,5c]thiazo-5(6H)-one
(7RS,7aR)-3-phenyl-6-(trimethylsily)-7-cyano-7,7a-dihydro-1H,3H-imidazo[1,5c]thiazo-5(6H)-one
(7RS,7aR)-3-phenyl-6-(2-propenyl)-7-cyano-7,7a-dihydro-1H,3H -imidazo[1,5c]thiazo-5(6H)-one
(7RS,7aR)-3-propyl-6benzyl-7-cyano-7,7a-dihydro-1H,3H-imidazo[1,5c]thiazo-5(6H)-one
(7RS,7aR)-3,3-idimethyl-6-benzyl-7-cyano-7,7a-dihydro-1H,3H-imidazo[1,5c]thiazo-5(6H)-one
(7RS,7aR)-3-ethyl-3-methyl-6-benzyl-7-cyano-7,7a-dihydro-1H,3H -imidazol[1,5c]thiazo-5(6H)-one
(7RS,7aR)-3-cyclohexyl-6-benzyl-7-cyano-7,7a-dihydro-1H,3H-imidazo[1,5c]thiazo-5(6H)-one
(7RS,7aR)-3,3-tetramethylenyl-6-benzyl-7-cyano-7,7a-dihydro-1H,3H-imidazo[1,5c]thiazo-5(6H)-one
(7RS,7aR)-3,3-pentamethylenyl-6-benzyl-7-cyano-7,7a-dihydro-1H,3H-imidazo[1,5c]thiazo-5(6H)-one

EXAMPLE 12

A solution of 7.92 g (0.12 mol) of 85% potassium hydroxide in 20 ml of water is added to a solution of 13.42 g (40 mmol) of a mixture of (7R,7aR)- and (7S,7aR)-3-phenyl-6-benzyl-7-cyano-7,7a-dihydro-1H,3H-imidazo[1,5-c]thiazol-5(6H)-one in 75 ml of n-butanol and the mixture is stirred at 100° C. for 90 minutes.

Most of the solvent is then distilled off, 200 ml of water are added and the mixture is extracted three times with 100 ml of methylene chloride each time.

Concentrated hydrochloric acid is added dropwise to the aqueous phase at 0° C. until pH 1 is reached and the product is filtered off with suction and rinsed in portions with a total of 100 ml of water.

13.5 g of (7R,7aR)-3phenyl-5(6H)-oxo-6-benzyl-7,7a-dihyro-1H,3H -imidazo[1,5-c]thiazole-7carboxylic acid with a melting point of 184°–185° C. are obtained.

$[\alpha]_{365}^{20} = =960°$, c=1 (methanol).

EXAMPLE 13

134.17 g (0.4 mol) of (7R,7aR)-3-phenyl-6-benzyl-7-cyano-7,7a-dihydro-1H,3H-imidazo[1,5-c]thiazol-5(6H)-one are suspended in 1000 ml of concentrated hydrochloric acid and the mixture is stirred at 80° C. for 3 hours. It is then cooled to 0° C., subsequently stirred for 3 hours and filtered with suction and the product is washed in portions with 500 ml of water.

129.8 g of (7R,7aR)-3-phenyl-5(6H)-oxo-6-benzyl-7,7a-dihydro-1H,3H-imidazo[1,5-c]thiazole-7-carboxylic acid with a melting point of 183°–184° C. are obtained.

$[\alpha]_{365}^{20} = -950°$, c=1 (methanol).

EXAMPLE 14

13.42 g (40 mmol) of (7S,7aR)-3-phenyl-6-benzyl-7-cyano-7,7a-dihydro-1H,3H-imidazo[1,5-c]thiazol-5(6H)-one and 100 ml of concentrated hydrochloric acid are reacted at 80° for 3 hours by the procedure described in Example 7. After the working-up described, (7S,7aR)-3-phenyl-5(6H)-oxo-6-benzyl-7,7a-dihydro-1H,3H-imidazo[1,5-c]thiazole-7-carboxylic acid is obtained; melting point: 220°–225° C.

EXAMPLE 15

134.17 g (0.4 mol) of a mixture of (7R,7aR)- and (7S,7aR)-3-phenyl-6-benzyl-7-cyano-7,7a-dihydro-1H,3H-imidazo[1,5-c]-thiazol-5(6H)-one are hydrolyzed with hydrochloric acid by the procedure described in Example 7. 127.2 g of a mixture of (7R,7aR)- and (7S,7aR)-3-phenyl-5(6H)-oxo-6-benzyl-7,7a-dihydro-1H,3H-imidazo[1,5-c]thiazole-7-carboxylic acid of no definite melting point are obtained.

EXAMPLE 16

32.64 g (0.1 mol) of (7RS,7aR)-3-phenyl-6-benzyl-7-cyano-7,7a-dihydro-7-hydroxy-1H,3H-imidazo[1,5- c]thiazol-5(6H)-one are added to a solution of 20.04 g (0.11 mol) of 1,1-sulfinyldiimidazole (W. Waiter, M. Radke; Liebigs Ann. Chem. 1979, 1756-67) in 350 ml of methylene chloride at room temperature under nitrogen.

The clear solution is stirred at room temperature for 30 minutes, washed twice with 150 ml of water each time, dried over sodium sulfate and filtered.

37.84 g (0.3 mol) of dimethyl sulfate are added dropwise to the filtrate at 10° C. (10 minutes) and the solution is stirred at 20° C. for 4 hours.

Excess dimethyl sulfate is then destroyed by addition of triethylamine at 20° C. and the mixture is concentrated under reduced pressure.

The oily residue is dissolved in 100 ml of dimethylformamide, 14.7 g (0.3 mol) of sodium cyanide are introduced and the reaction mixture is stirred at 85° C. for 60 minutes.

The reaction mixture is then stirred into 500 ml of ice-water and extracted three times with 150 ml of ethyl acetate each time. The combined organic phases are washed with water and saturated sodium chloride solution and concentrated under reduced pressure. The resulting nitrile is hydrolyzed in a manner analogous to that described in Example 6, using 200 ml of n-butanol, 19.8 g (0.3 mol) of 85% potassium hydroxide and 40 ml of water.

22.68 g of (7R,7aR)-3-phenyl-5(6H)-oxo-6-benzyl-7,7a-dihydro-1H,3H-imidazo[1,5-c]thiazole-7-carboxylic acid are obtained, melting point: 180°-181° C., $[\alpha]_{365}^{20} = -945°$, c=1, methanol.

EXAMPLE 17

7.32 g (112 mmol) of zinc powder are added in portions to a solution of 9.92 g (28 mmol) of (7R,7aR)-3-phenyl-5(6H)-oxo-6-benzyl-7,7a-dihydro-1H,3H-imidazo[1,5-c]-thiazole-7-carboxylic acid in 150 ml of anhydrous acetic acid at 80° C., the mixture is stirred at 80° C. for a further 4 hours and filtered and the filtrate is concentrated under reduced pressure.

The residue is dissolved in 500 ml of ethyl acetate and the solution is washed with 200 ml of water and 100 ml of saturated sodium chloride solution, dried over sodium sulfate and concentrated under reduced pressure. The product crystallizes on trituration with diethyl ether.

9.39 g of (4R,5R)-1,3-dibenzyl-2-oxo-5-mercaptomethyl-imidazolidine-4-carboxylic acid with a melting point of 167°-169° C. are obtained.

$[\alpha]_{365}^{20} = +83°$, c=1 (methanol).

EXAMPLE 18

7.32 g (112 mmol) of zinc powder are added, a little at a time, to a solution of 9.92 g (28 mmol) of (7R,7aR)-3-phenyl-5-(6H)-oxo-6-benzyl-7,7a-dihydro-1H,3H-imidazo, 1,5-c]thiazole-7-carboxylic acid in a mixture of 100 ml of anhydrous acetic aicd and 4.29 g (42 mmol) of acetic anhydride at 90° C., and the mixture is then stirred for 2 hours at 110° C.

It is then cooled to 60° C., filtered and concentrated under reduced pressure.

The residue is suspended in 120 ml of water, the suspension is stirred for 60 minutes at room temperature and is filtered, and the residue is dried in vacuo.

9.5 g of (4R,5R)-1,3-dibenzyl-2-oxo-5-acetylmercaptomethyl-imidazoline-4-carboxylic acid, with a melting point of 135°-140° C., are obtained.

$[\alpha]_{365}^{20} = +173°$, c=1 (methanol).

EXAMPLE 19

35.64 g (0.1 mol) of (4R,5R)-1,3-dibenzyl-2-oxo-5-mercaptomethyl-imidazoline-4-carboxylic acid are dissolved in 300 ml of dimethylacetamide, 13.61 g (0.1 mol) of sodium acetate trihydrate are introduced and the mixture is heated at 150° C. for 40 minutes.

It is then cooled to room temperature, stirred into 900 ml of water and extracted four times with 100 ml of toluene each time. The combined organic phases are washed three times with 50 ml of water each time and once with 50 ml of saturated sodium chloride solution and concentrated under reduced pressure. The residue is recrystallized from ethyl acetate.

28.76 g of (3aS,6aR)-1,3-dibenzyl-tetrahydrothieno[3,4-d]imidazole-2(3H),4-dione with a melting point of 118°-119° C. are obtained.

$[\alpha]_D^{20} = +90.8°$, c=1 (CHCL$_3$).

EXAMPLE 20

39.85 g (0.1 mol) of (4R,5R)-1,3-dibenzyl-2-oxo-5-acetylmercaptomethyl-imidazoline-4-carboxylic acid are dissolved in 100 ml of dimethylformamide, 11.42 g (0.1 mol) of potassium thioacetate are introduced and the reaction mixture is heated for 2 hours at 130° C.

It is then cooled to room temperature and stirred into 800 ml of water, and the mixture is extracted four times with 100 ml of toluene at a time. The combined organic phases are washed three times with 50 ml of water at a time and once with saturated sodium chloride solution, and are evaporated under reduced pressure.

The residue is recrystallized from 2-propanol, giving 25.4 g of (3aS,6aR)-1,3-dibenzyl-tetrahydrothieno[3,4-d]-imidazole-2(3H),4-dione, with a melting point of 118° C.

$[\alpha]_D^{20} = +90.7°$, c=1 (CHCL$_3$).

EXAMPLE 21

A solution of 39.85 g (0.1 mol) of (4R,5R)-1,3-dibenzyl-2-oxo-5-acetylmercaptomethyl-imidazoline-4-carboxylic acid in 300 ml of 1 N sodium hydroxide solution is stirred for 60 minutes at room temperature, then acidified to pH 4 with concentrated hydrochloric acid and extracted three times with 100 ml of methylene chloride at a time. The combined organic phases are dried over sodium sulphate and concentrated under reduced pressure.

The residue is dissolved in 100 ml of N-methylpyrrolidone, 11.42 g (0.1 mol) of potassium thioacetate are introduced and the reaction mixture is heated for 90 minutes at 130° C.

It is then cooled to room temperature and stirred into 800 ml of water, and the mixture is extracted four times with 100 ml of toluene at a time. The combined organic phases are washed three times with 50 ml of water at a time and once with saturated sodium chloride solution, and are evaporated under reduced pressure.

The residue is recrystallized from 2-propanol, giving 22.6 g of (3aS,6aR)-1,3-dibenzyl-tetrahydrothieno[3,4-d]-imidazole-2(3H),4-dione, with a melting point of 119°-120° C.

$[\alpha]_D^{20} = +91.4°$, c=1 (methanol).

EXAMPLE 22

100 ml of a one-molar solution of potassium hydroxide in methanol are added to a solution of 39.85 g (0.1 mol) of (4S,5R)-1,3-dibenzyl-2-oxo-5-acetylmercaptomethyl-imidazolin-4-carboxylic acid in 200 ml of methanol and the mixture is concentrated under reduced pressure.

The oily residue is dissolved in 100 ml of dimethylformamide and the solution is heated for 3 hours at 130° C.

It is then cooled to room temperature and stirred into 800 ml of water, and the mixture is extracted four times with 100 ml of toluene at a time. The combined organic phases are washed three times with 50 ml of water at a time and once with saturated sodium chloride solution, and are concentrated under reduced pressure.

The residue is recrystallized from 2-propanol, giving 27.7 g (3aS,6aR)-1,3-dibenzyltetrahydrothieno[3,4-d]-imidazole-2(3H)-4-dione, with a melting point of 119° C.

$[\alpha]_D^{20} = +91.1°, c = 1$ (CHCL$_3$).

EXAMPLE 23

39.85 g (0.1 mol) of (4R,5R)-1,3-dibenzyl-2-oxo-5-acetylmercaptomethyl-imidazoline-4-carboxylic acid are dissolved in 100 ml of N-methylpyrrolidone, 11.22 g (0.2 mol) of potassium tert.-butylate are introduced and the reaction mixture is heated for 2 hours at 130° C.

The mixture is then cooled to room temperature and stirred into 800 ml of water, and the batch is extracted four times with 100 ml of toluene at a time. The combined organic phases are washed three times with 50 ml of water at a time and are concentrated under reduced pressure.

The residue is recrystallized from 2-propanol, giving 28.3 g of (3aS,6aR)-1,3-dibenzyltetrahydrothieno[3,4-d]-imidazole-2(3H),4-dione, with a melting point of 118°-119° C.

$[\alpha]_D^{20} = +90.8°, c = 1$ (CHCL$_3$).

EXAMPLE 24

Following the procedure described in Example 23, 39.85 g (0.1 mol) of (4R,5R)-1,3-dibenzyl-2-oxo-5-acetylmercaptomethyl-imidazolin-4-carboxylic acid are reacted with 5.40 g (0.1 mol) of sodium methylate in 100 ml of N-methylpyrrolidone.

28.0 g of (3aS,6aR)-1,3-dibenzyltetrahydrothieno[3,4-d]imidazol-2(3H),4-dione, with a melting point of 119°-120° C., are obtained.

$[\alpha]_D^{20} = +91.3°, c = 1$ (CHCL$_3$).

EXAMPLE 25

Following the procedure described in Example 23, 39.85 g (0.1 mol) of (4R,5R)-1,3-dibenzyl-2-oxo-5-acetylmercaptomethyl-imidazoline-4-carboxylic acid are reacted with 4.0 g (0.1 mol) of sodium hydroxide in 100 ml of N-methylpyrrolidone.

22.9 g of (3aS,6aR)-1,3-dibenzyl-tetrahydrothieno[3,4-d]-imidazole-2(3H),4-dione, with a melting point of 119° C., are obtained.

$[\alpha]_D^{20} = +90.8°, c = 1$ (CHCL$_3$).

EXAMPLE 26

1.43 g of (7.5 mmol) of toluene-4-sulphonic acid monohydrate and 37.14 g (0.18 mol) of N,N'-dicyclohexylcarbodiimide are added to a solution of 53.47 g (0.15 mol) of (4R,5S)-1,3-dibenzyl-2-oxo-5-mercaptomethylimidazoline-4-carboxylic acid in 300 ml of pyridine at room temperature and the mixture is stirred for 6 hours at 20° C.

It is then filtered and the filtrate is concentrated under reduced pressure.

The residue is dissolved in 400 ml of toluene, the solution is washed twice with 50 ml of 1 N hydrochloric acid at a time and is concentrated, and the residue is recrystallized from 2-propanol.

40.6 g of (3aS,6aR)-1,3-dibenzyltetrahydrothieno[3,4-d]-imidazole-2(3H),4-dione, with a melting point of 119°-120° C., are obtained.

$[\alpha]_D^{20} = +91.3°, c = 1$ (CHCL$_3$).

EXAMPLE 27

1.70 g (18 mmol) of methyl chloroformate are added to a solution of 5.35 g (15 mmol) of (4R,5R)-1,3-dibenzyl-2-oxo-5-mercaptomethyl-imidazoline-4-carboxylic acid in a mixture of 50 ml of methylene chloride and 1.42 g (18 mmol) of pyridine at 5° C. and the mixture is boiled for 36 hours under reflux.

It is then cooled to room temperature, washed twice with 25 ml of 1 N hydrochloric acid at a time, dried over sodium sulphate and concentrated under reduced pressure.

The residue is chromatographed on slilica gel, using toluene/ethyl acetate (9:1, v/v).

3.1 g of (3aS,6aR)-1,3-dibenzyltetrahydrothieno[3,4-d]-imidazole-2(3H),4-dione, with a melting point of 119° C., are obtained.

$[\alpha]_D^{20} = +90.9°, c = 1$ (CHCL$_3$).

EXAMPLE 28

7.32 g (112 mmol) of zinc powder are added in portions to a solution of 9.92 g (28 mmol) of (7S,7aR)-3-phenyl-5(6H)-oxo-6-benzyl-7,7a-dihydro-1H,3H-imidazo[1,5c]-thiazole-7-carboxylic acid in 150 ml of anhydrous acetic acid at 80° C., the mixture is stirred at 80° C. for a further 4 hours and filtered and the filtrate is concentrated under reduced pressure.

The residue is dissolved in 300 ml of toluene and the solution is washed with 150 ml of water and 75 ml of saturated sodium chloride solution and concentrated under reduced pressure. The crude thiolactone is recrystallized from ethyl acetate.

8.0 g of (3aS,6aR)-1,3-dibenzyl-tetrahydrothieno[3,4-d]-imidazole-2(3H),4-dione with a melting point of 119°-120° C. are obtained.

$[\alpha]_D^{20} = +91.2°, c = 1$ (CHCL$_3$).

EXAMPLE 29

73.22 g (1.12 mol) of zinc powder are added in portions to a solution of 99.24 g (0.28 mol) of (7R,7aR)- and (7S,7aR)-3-phenyl-5(6H)-oxo-6-benzyl-7,7a-dihydro-1H,3H-imidazo-[1,5-c]thiazole-7-carboxylic acid in 1500 ml of anhydrous acetic acid at 80° C., the mixture is stirred at 80° C. for a further 4 hours and filtered and the filtrate is concentrated under reduced pressure.

The residue is dissolved in 1000 ml of dimethylformamide, 38.1 g (0.28 mol) of sodium acetate trihydrate are added to the solution and the mixture is stirred at 125° C. for 60 minutes.

It is then cooled to room temperature, stirred into 1500 ml of water and extracted four times with 200 ml of toluene each time and the combined extracts are washed three times with 150 ml of water each time and once with saturated sodium chloride solution and concentrated under reduced pressure.

The residue is recrystallized from ethyl acetate to give 75.8 g of (3aS,6aR)-1,3-dibenzyl-tetrahydrothieno[3,4-d]-imidazole-2(3H),4-dione with a melting point of 118°-119° C.

$[\alpha]_D^{20} = +90.6°, c = 1$ (CHCL$_3$).

EXAMPLE 30

10.06 g (30 mmol) of (7S,7aR)-3-phenyl-6-benzyl-7-cyano-7,7a-dihydro-1H,3H-imidazo[1,5c]thiazol-5(6H)-one are suspended in 150 ml of saturated methanolic hydrochloric acid and the mixture is stirred at 60° C. for 5 hours.

It is then cooled, 500 ml of ice-water are added and the mixture is extracted four times with 150 ml of ethyl acetate each time.

The combined organic phases are washed with a total of 300 ml of water, dried over sodium sulfate and concentrated under reduced pressure. The product crystallizes on trituration with diethyl ether.

10.2 g of methyl (7S,7aR)-3-phenyl-5(6H)-oxo-6-benzyl-7,7a-dihydro-1H,3H-imidazo[1,5-c]thiazole-7-carboxylate with a melting point of 155°–156° C. are obtained.

$[\alpha]_{365}^{20} = -752°$, c=1 (methanol).

EXAMPLE 31

10.1 g of methyl (7R,7aR)-3-phenyl-5(6H)-oxo-6-benzyl-7,7a-dihydro-1H-3H-imidazo[1,5-c]thiazole-7-carboxylate are obtained as a colourless oil from 10.06 g (30 mmol) of (7R,7aR)-3-phenyl-6-benzyl-7-cyano-7,7a-dihydro-1H,3H-imidaxo[1,5-c]thiazol-5(6H)-one by the procedure described in Example 15;

$[\alpha]_{365}^{20} = -862°$, c=1 (methanol).

EXAMPLE 32

7.85 g (120 mmol) of zinc powder are added in portions to a solution of 11.05 g (30 mmol) of methyl (7S,7aR)-3-phenyl-5(6H)-oxo-6-benzyl-7,7a-dihydro-1H,3H-imidaz-[1,5-c]thiazole-7-carboxylate in 150 ml of anhydrous acetic acid at 80° C., the mixture is stirred at 80° C. for a further 4 hours and filtered and the filtrate is concentrated under reduced pressure.

The residue is dissolved in 300 ml of toluene and the solution is washed with 150 ml of water and 75 ml of saturated sodium chloride solution and concentrated under reduced pressure.

The crude thiolactone is recrystallized from ethyl acetate. 8.4 g of (3aS,6aR)-1,3-dibenzyl-tetrahydro-thieno-[3,4-d]imidazole-2(3H),4-dione with a melting point of 120° C. are obtained.

$[\alpha]_D^{20} = +91.1°$, c=1 (CHCL$_3$).

EXAMPLE 33

7.85 g (120 mmol) of zinc powder are added in portions to a solution of 11.05 g (30 mmol) of methyl (7R,7aR)-3-phenyl-5(6H)-oxo-6-benzyl-7,7a-dihydro-1H,3H-imidazo[1,5-c]-thiazole-7-carboxylate in 150 ml of anhydrous acetic acid at 80° C., the mixture is stirred at 80° C. for a further 4 hours and filtered and the filtrate is concentrated under reduced pressure.

The residue is dissolved in 110 ml of dimethylformamide, 4.08 g (30 mmol) of sodium acetate trihydrate are added to the solution and the mixture is stirred at 110° C. for 60 minutes.

The mixture is then cooled to room temperature, stirred into 200 ml of water and extracted four times with 100 ml of toluene each time and the combined extracts are washed three times with 50 ml of water each time and once with 50 ml of saturated sodium chloride solution and concentrated under reduced pressure.

The residue is recrystallized from ethyl acetate to give 7.5 g of (3aS,6aR)-1,3-dibenzyl-tetrahydro-thieno[3,4-d]-imidazole-2(3H),4-dione with a melting point of 119° C.

$[\alpha]_D^{20} = -90.6°$, c=1 (CHCL$_3$).

EXAMPLE 34

A Grignard reagent solution prepared from 3.68 g (30 mmol) of 1-chloro-4-methoxybutane and 0.97 g (40 mmol) of magnesium in 15 ml of tetrahydrofuran is added dropwise to a solution of 6.71 g (20 mmol) of (7R,7aR)-3-phenyl-6-benzyl-7-cyano-7,7a-dihydro-1H,3H-imidazo[1,5-c]thiazol-5(6H)-one in 10 ml of tetrahydrofuran at 40° C. under nitrogen.

The mixture is stirred at 40° C. for 30 minutes, 50 ml of ice-water are added and the pH is brought to 4 with 1 N hydrochloric acid. The mixture is then extracted three times with 50 ml of ether each time and the extract is dried over sodium sulfate and concentrated under reduced pressure. The crude product is chromatographed on silica gel with diethyl ether.

6.6 g of (7R,7aR)-3-phenyl-6-benzyl-7-(5-methoxypentanoyl)-7,7a-dihydro-1H,3H-imidazo[1,5-c]thiazol-5(6H)-one are obtained as a yellow oil.

$[\alpha]_{436}^{20} = -480°$, c=1 (methanol).

EXAMPLE 35

3.86 g (30 mmol) of 1-chloro-4-methoxybutane, 0.97 g (40 mmol) of magnesium and 6.71 g (20 mmol) of (7S,7aR)-3-phenyl-6-benzyl-7-cyano-7,7a-dihydro-1H,3H-imidazo[1,5-c]-thiazol-5(6H)-one are reacted with one another in 25 ml of tetrahydrofuran by the procedure described in Example 19.

6.3 g of (7R,7aR)-3-phenyl-6-benzyl-7-(5-methoxypentanoyl)-7,7a-dihydro-1H,3H-imidazo[1,5-c]thiazol-5(6H)-one are obtained as a yellow oil.

$[\alpha]_{436}^{20} = -475°$, c=1 (methanol).

EXAMPLE 36

7.06 g (108 mmol) of zinc powder are added in portions to a solution of 11.46 g (27 mmol) of (7R,7aR)-3-phenyl-6-benzyl-7-(5-methoxypentanoyl)-7,7a-dihydro-1H,3H-imidazo[1,5-c]thiazol-5(6H)-one in 200 ml of anhydrous acetic acid at 80° C., the mixture is stirred at 80° C. for a further 5 hours and filtered, and the filtrate is concentrated under reduced pressure.

The residue is taken up in 150 ml of toluene and the mixture is washed three times with 100 ml of water each time and concentrated again under reduced pressure. (4R,5R)-1,3-Dibenzyl-2-oxo-4-(5-methoxypentanoyl)-5-mercaptomethylimidazolidine is obtained as the residue;

$[\alpha]_{365}^{20} = -52.6°$, c=1 (methanol).

The pale yellow oil is dissolved in 3.66 g (61 mmol) of anhydrous acetic acid at room temperature, 5.19 g (61 mmol) of piperidine are added dropwise, while cooling with ice, and the melt is heated at 100° C. for 90 minutes, with stirring.

The mixture is then cooled to 20° C., 150 ml of water are added and the mixture is extracted three times with 100 ml of tert.-butyl methyl ether each time. The combined organic phases are washed with 1 N hydrochloric acid and water, dried over sodium sulfate and concentrated under reduced pressure.

A solution of the oily residue in 50 ml of acetic acid is then heated at 100° C. for 2 hours, cooled and concentrated under reduced pressure.

The residue is taken up in 100 ml of tert.-butyl methyl ether, the mixture is washed once with 50 ml of 2 N sodium hydroxide solution and then twice with 50 ml of water each time, dried over sodium sulfate and concentrated and the crude product is chromatographed on silica gel (diethyl ether).

8.1 g of (3aS,6aR)-1,3-dibenzyl-4-(4-methoxybutylidene)-tetrahydro-thieno[3,4-d]imidazol-2(3H)-one are obtained as an oil.

$[\alpha]_D^{25} = +236°$, c=1 (benzene).

EXAMPLE 37

57.5 ml (92 mmol) of a 1.6 molar solution of n-butyllithium in n-hexane are added dropwise to a suspension, stirred under nitrogen, of 19.95 g (45 mmol) of (4-carboxybutyl)-triphenylphosphonium bromide in 120 ml of tetrahydrofuran at 20° C.

The mixture is stirred at room temperature for 40 minutes and cooled to 0° C., 7.36 g (55 mmol) of lithium iodide are introduced and a solution of 13.42 g (40 mmol) of a mixture of (7R,7aR)- and (7S,7aR)-3-phenyl-6-benzyl-7-cyano-7,7a-dihydro-1H,3H-imidazol[1,5-c]thiazol-5(6H)-one in 75 ml of THF is added dropwise in the course of 20 minutes.

The mixture is subsequently stirred at room temperature for one hour and then at 50° C. for 2 hours and is cooled to 0° C., and a mixture of 30 ml of ice-water and 25 ml of concentrated hydrochloric acid is added.

The mixture is stirred at room temperature for 30 minutes and most of the solvent is distilled off under reduced pressure. The residue is taken up in 150 ml of ethyl acetate.

After separation of the phases, the organic solution is washed twice with 50 ml of water each time, dried over sodium sulfate and concentrated under reduced pressure.

The residue is dissolved in 150 ml of anhydrous acetic acid, and 7.85 g (120 mmol) of zinc powder are added in portions at 80° C. The mixture is stirred at 90° C. for 4 hours and filtered and the filtrate is concentrated under reduced pressure.

The oily residue is taken up in 100 ml of toluene and the mixture is washed three times with 50 ml of water each time and concentrated again under reduced pressure. (4R,5R)-1,3-Dibenzyl-2-oxo-4-(5-carboxypentanoyl)-5-mercapto-methyl-imidazolidine is obtained as the residue.

To dissolve the residue in 7.21 g (120 mmol) of acetic acid, 11.92 g (140 mmol) of piperidine are added dropwise at 0° C. and the mixture is heated at 100° C. for 2 hours.

It is then cooled to 25° C., 150 ml of water are added, the pH brought to 3 with 2 N hydrochloric acid and the mixture is extracted three times with 100 ml of ethyl acetate each time. The combined organic solutions are washed with 1 N hydrochloric acid and water, dried over sodium sulfate and concentrated under reduced pressure. (3aS,4RS,6aR)-1,3-Dibenzyl-4-hydroxy-4-(4-carboxybutyl)-tetrahydro-thieno[3,4-d]imidazol-2(3H)-one is obtained as the residue.

A solution of the oily residue in 75 ml of acetic acid is then heated at 100° C. for 1 hour, cooled to room temperature and concentrated under reduced pressure.

The residue is taken up in 150 ml of ethyl acetate, the mixture is washed twice with 50 ml of water each time, dried over sodium sulfate and concentrated and the crude product is chromatographed on silica gel (toluene/ethyl acetate 3:1, volume/volume).

10.1 g of (3aS,6aR)-1,3-dibenzyl-4-(4-carboxybutylidene)-tetrahydrothieno[3,4-d]imidazol-2(3H)-one with a melting point of 79°–82° C. are obtained.

$[\alpha]_D^{22} = +215°$, c=1 (methanol).

EXAMPLE 38

A solution of 12.40 g (66 mmol) of 1,2-dibromoethane in 18 ml of diethyl ether is added dropwise over 15 minutes, at 23° to 27° C., to a suspension, stirred under nitrogen, of 5.49 g (226 mmol) of magnesium shavings in a mixture of 35 ml of diethyl ether and 35 ml of toluene, the mixture is stirred for 45 minutes at room temperature and a solution of 8.38 g (66 mmol) of 1,4-dichlorobutane in a mixture of 18 ml of diethyl ether and 38 ml of toluene is then added dropwise over 25 minutes, without cooling.

Stirring is continued for 90 minutes, the mixture is cooled to −30° C., and at this temperature a solution of 7.38 g (22 mmol) of (7RS,7aR)-3-phenyl-6-benzyl-7-cyano-7,7a-dihydro-1H,3H-imidazo[1,5-c]-thiazol-5(6H)-one in 150 ml of toluene is added dropwise over 30 minutes.

Carbon dioxide is then passed in over 60 minutes, during which the temperature is allowed to rise to 0° C. The mixture is then concentrated under reduced pressure and the residue is partitioned between 150 ml of 1 N hydrochloric acid and 200 ml of ethyl acetate. The organic phase is separated off, dried over sodium sulphate and concentrated under reduced pressure.

6.05 g of (7RS,7aR)-3-phenyl-6-benzyl-7-(5-carboxypentanoyl)-7,7a-dihydro-1H,3H-imidazo[1,5-c]-5-(6H)-one are obtained as an oil which is laevo-rotatory in methanol.

The residue is dissolved in 100 ml of anhydrous acetic acid and 5.88 g (90 mmol) of zinc powder are added, a little at a time, at 80° C. The mixture is stirred for 4 hours at 90° C., filtered and concentrated under reduced pressure.

The residue is dissolved in 5.40 g (90 mmol) of acetic acid, 8.52 g (100 mmol) of piperidine are added dropwise at 0° C. and the mixture is heated for 2 hours at 100° C.

It is then cooled to 25° C., 100 ml of water are added, the pH is brought to 3 with 2 N hydrochloric acid and the mixture is extracted three times with 50 ml of ethyl acetate at a time.

The combined organic solutions are washed with 1 N hydrochloric acid and water, dried over sodium sulphate and concentrated under reduced pressure.

(3aS,4RS,6aR)-1,3-Dibenzyl-4-hydroxy-4-(4-carboxybutyl)-tetrahydrothieno[3,4-d]imidazol-2(3H)-one is obtained as the residue, in the form of an oil which is laevo-rotatory in methanol.

The solution of the residue in 50 ml of acetic acid is then heated for 1 hour at 100° C. and concentrated under reduced pressure. The residue is taken up in 100 ml of ethyl acetate, the solution is washed twice with 50 ml of water at a time, dried over sodium sulphate and concentrated, and the crude product is chromatographed on silica gel (toluene/ethyl acetate 3:1, v/v).

4.2 g of (3aS,6aR)-1,3-dibenzyl-4-(4-carboxybutylidene)-tetrahydrothieno[3,4-d]imidazol-2(3H)-one, with a melting point of 80°–82° C., are obtained.

$[\alpha]_D^{22} = +214°$, c=1 (methanol).

EXAMPLE 39

A solution of 19.43 g (90 mmol) of 1,4-dibromobutane in 240 ml of diethyl ether is added dropwise, over 30 minutes, to a suspension, stirred under nitrogen, of 7.53 g (310 mmol) of magnesium shavings in 50 ml of diethyl ether, the mixture is boiled for 60 minutes under reflux and a solution of 10.06 g (30 mmol) of (7RS,7aR)-3-phenyl-6-benzyl-7-cyano-7,7a-dihydro-1H,3H-imidazo[1,5-c]thiazol-5(6H)-one in 300 ml of diethyl ether is then added dropwise at 30° C. over 10 minutes.

The reaction mixture is then cooled to −30° C. and carbon dioxide is passed in over 60 minutes, with the temperature being allowed to rise to 0° C.

The solvent is distilled off and the residue is partitioned between 200 ml of 1 N hydrochloric acid and 200 ml of ethyl acetate. The organic phase is separated off, dried over sodium sulphate and concentrated under reduced pressure. 7.2 g of (7RS,7aR)-3-phenyl-6-benzyl-7-(5-carboxypentanoyl)-7,7a-dihydro-1H,3H-imidazo[1,5-c]-thiazol-5(6H)-one are obtained as an oil which is laevo-rotatory in methanol.

The residue is dissolved in 150 ml of anhydrous acetic acid and 6.54 g (100 mmol) of zinc powder are added, a little at a time, at 80° C. The mixture is stirred for 4 hours at 90° C. and is filtered, and 140 ml of acetic acid are distilled off.

After addition of 17.03 g (200 mmol) of piperidine at 0° C., the reaction mixture is heated for 2 hours at 100° C., 150 ml of acetic acid are then added, stirring is continued for 60 minutes at 100° C. and the mixture is concentrated under reduced pressure.

The residue is taken up in 150 ml of ethyl acetate and the solution is washed with 1 N hydrochloric acid and water, dried over sodium sulphate and concentrated under reduced pressure.

(3aS,6aR)-1,3-Dibenzyl-4-(4-carboxybutylidene)-tetrahydrothieno[3,4-d]imidazol-2(3H)-one is obtained as the residue.

The crude product is dissolved in 40 ml of methanol, 30 ml of a saturated solution of hydrogen chloride in methanol are added and the resulting solution is stirred for 2 hours at room temperature. The mixture is then concentrated under reduced pressure and the oily residue is taken up in 100 ml of toluene.

The solution is washed twice with 50 ml of water at a time, the solvent is distilled off and the crude product is chromatographed on silica gel (toluene/ethyl acetate 9:1, v/v).

6.4 g of (3aS,6aR)-1,3-Dibenzyl-4-(4-methoxycarbonylbutylidene)-tetrahydrothieno[3,4-d]imidazol-2(3H)-one are obtained as an oil.

$[\alpha]_D^{25} = +227°$, c=1 (benzene).

EXAMPLE 40

Using the procedure described in Example 39, 19.43 g (90 mmol) of 1,4-dibromobutane, 7.53 g (310 mmol) of magnesium and 10.06 g (30 mmol) of (7R,7aR)-3-phenyl-6-benzyl-7-cyano-7,7a-dihydro-1H,3H-imidazo[1,5-c]thiazol-5(6H)-one are reacted in 290 ml of diethyl ether.

6.8 g of (3aS,6aR)-1,3-dibenzyl-4-(4-methoxycarbonylbutylidene)-tetrahydrothieno[3,4-d]imidazol-2(3H)-one is obtained as an oil.

$[\alpha]_D^{25} = +225°$, c=1 (benzene).

EXAMPLE 41

Using the procedure described in Example 39, 19.43 g (90 mmol) of 1,4-dibromobutane, 7.53 g (310 mmol) of magnesium and 10.06 g (30 mmol) of (7S,7aR)-3-phenyl-6-benzyl-7-cyano-7,7a-dihydro-1H,3H-imidazo[1,5-c]thiazol-5(6H)-one are reacted in 290 ml of diethyl ether.

5.2 g of (3aS,6aR)-1,3-Dibenzyl-4-(4-methoxycarbonylbutylidene)-tetrahydrothieno[3,4-d]imidazol-2(3H)-one are obtained as an oil.

$[\alpha]_D^{25} = +223°$, c=1 (benzene).

EXAMPLE 42

200 ml of a 1M solution of diisobutylaluminium hydride in toluene are added dropwise to a solution of 33.54 g (0.1 mol) of a mixture of (7R,7aR)- and (7S,7aR)-3-phenyl-6-benzyl-7-cyano-7,7a-dihydro-1H,3H-imidazo[1,5-c]thiazol-5(6H)-one in 250 ml of toluene at −70° C. under nitrogen, the mixture is warmed to 0° C. in the course of 3 hours and this temperature is maintained for a further 2 hours. 5 ml of methanol are then added and the mixture is stirred into 250 ml of saturated ammonium chloride solution. The phases are separated and the organic phase is then extracted by shaking with 100 ml of 10% sulfuric acid for 20 minutes.

The phases are separated and the organic phase is washed twice with 100 ml of water each time, dried over sodium sulfate and concentrated under reduced pressure.

29.4 g of a mixture of (7R,7aR)- and (7S,7aR)-3-phenyl-5(6H)-oxo-6-benzyl-7,7a-dihydro-1H,3H-imidazo[1,5-c]thiazole-7-carbaldehyde are obtained.

EXAMPLE 43

57.5 ml (92 mmol) of a 1.6 M solution of n-butyllithium in n-hexane are added dropwise to a suspension, stirred under nitrogen, of 19.95 g (45 mmol) of (4-carboxybutyl)-triphenylphosphonium bromide in 150 ml of tetrahydrofuran at 20° C.

The reaction mixture is stirred at 20° C. for 60 minutes and cooled to 0° C., a solution of 13.54 g (40 mmol) of a mixture of (7R,7aR)- and (7S,7aR)-2-oxo-3-phenyl-6-benzyl-7,7a-dihydro-1H,3H,6H-imidazo[1,5-c]thiazole-7-carbaldehyde in 50 ml of tetrahydrofuran is added dropwise in the course of 15 minutes. After a further 60 minutes, the reaction mixture is stirred into 200 ml of ice-water and brought to pH 2 with concentrated hydrochloric acid. The phases are separated and the aqueous phase is extracted with twice 50 ml of ethyl acetate. The combined organic phases are washed with water and saturated sodium chloride solution, dried over sodium sulfate and concentrated under reduced pressure. The crude product is then chromatographed with ethyl acetate on silica gel.

13.9 g of a mixture of (7R,7aR)- and (7S,7aR)-3-phenyl-6-benzyl-(5-carboxy-pent-1-enyl)-7,7a-dihydro-1H,3H-imidazo-[1,5-c]thiazol-5(6H)-one are obtained as an oil.

EXAMPLE 44

7.85 g (120 mmol) of zinc powder are added in portions to a solution of 12.68 g (30 mmol) of a mixture of (7R,7aR)-and (7S,7aR)-3-phenyl-6-benzyl-(5-carboxypent-1-enyl)-7,7a-dihydro-1H,3H-imidazo[1,5-c]thiazol-5(6H)-one in 150 ml of anhydrous acetic acid at 85° C., the mixture is stirred at 85° C. for a further 4 hours and filtered and the filtrate is concentrated under reduced pressure. The residue is chromatographed on silica gel (methylene chloride/methanol 9:1, volume/volume).

4.8 g of (3aS,4S,6aR)-1,3-dibenzyl-4-(4-carboxybutyl)-tetrahydro-thieno[3,4-d]imidazol-2(3H)-one with a melting point of 88°–89° C. are obtained.

$[\alpha]_D^{22} = -24.3°$, c=1 (methanol).

EXAMPLE 45

8.77 g (20 mmol) of a mixture, obtained using the procedure described in Examples 38-41, of (7S,7aR)- and (7R,7aR)-3-phenyl-6-benzyl-7-(5-carboxypentanoyl)-7,7a-dihydro-1H,3H-imidazo[1,5-c]thiazol-5(6H)-one are dissolved in 60 ml of methanol and 40 ml of a saturated solution of hydrogen chloride in methanol are added.

The mixture is stirred for 2 hours at room temperature and concentrated under reduced pressure. The residue is dissolved in 100 ml of toluene, the solution is washed twice with 50 ml of water at a time, the solvent is distilled off and the crude product is chromatographed on silica gel (ethyl acetate).

3.3 g of (3aS,6aR)-3-benzyl-4-(4-methoxycarbonylbutylidene)-tetrahydrothieno[3,4-d]imidazol-2(3H)-one are obtained as an oil.

$[\alpha]_D^{25} = +215°$, c=1 (methanol).

What is claimed is:

1. A process for the preparation of D-(+)-biotin, comprising:
   (i) Reducing a starting material compound of the formula

[structure]

wherein
   $R^1$ and $R^2$ are each in independently H, alkyl, substituted alkyl, cycloalkyl, aryl, aralkyl or heteroaryl, wherein the heteroatom is O, N, or S, or taken together are alkylene, substituted alkylene or heteroalkylene, wherein the heteroatom is O, N, or S;
   $R^3$ is H or benzyl, benzyl substituted by one or more of $C_{1-4}$-alkyl, $C_{1-4}$-alkoxyl, $C_{3-5}$alkyl-2-enyl or $C_{3-6}$-trialkylsilyl;
   X and Y independently are each O or S;
   to an alcohol of the formula

[structure]

by reacting said starting material compound with a reducing agent or by catalytically hydrogenating said starting material compound;
   (ii) converting said alcohol into an activated ester of the formula

[structure]

wherein $R^4$ is an activating ester group and is alkanoyl, aroyl, alkylsulfonyl or azole.M, wherein azole is a fused or non-fused, substituted or unsubstituted, nitrogen-containing 5-membered ring, and M is CO, CS, $SO_2$, SO or S;
   (iii) reacting said activated ester with an alkali metal cyanide, an alkaline earth metal cyanide or a cyanosilane, to give a nitrile of the formula

[structure]

(iv) reacting the product of step (iii) with a reducing agent to give an aldehyde of the formula

[structure]

(v) condensing said aldehyde with an organophosphorus compound to give an unsaturated carboxylic acid of the formula

[structure]

wherein Z is $OR^5$ or $COOR^5$, wherein $R^5$ is H, alkyl, cycloalkyl or aryl;
   (vi) reacting said carboxylic acid with an acid, a reducing agent or a mixture thereof to produce a biotin derivative of the formula

[structure]

wherein $R^6$ is H or $R^1R^2CH$;
   (vii) converting said derivative into D-(+)-biotin by known processes.

2. A process according to claim 1, wherein in said catalytic hydrogenation, the catalyst is a noble metal or noble metal oxide.

3. A process according to claim 2, wherein the hydrogenation is carried out at a temperature of about 0°–200° C. and a pressure of 1–200 bar.

4. A process according to claim 1, wherein in step (ii) the activated ester is produced by reacting said alcohol with a compound $R^4$—Q, wherein Q is halogen, alkoxy, alkanoyloxy or azole as defined for $R^4$.

5. A process according to claim 4, wherein the reaction with said compound $R^4$—Q is performed in the presence of a base consisting essentially of triethylamie, pyridine, lutidine, coolidine, quinoline or a mixture thereof, and is performed at a temperature of about −50° to +150° C.

6. A process according to claim 1, wherein in step (iii) the ester is reacted with sodium cyanide, potassium cyanide, copper cyanide, trimethylislyl cyanide, β-triethylsilyprpoionitrile or diethylaluminum cyanide, and wherein the reaction with said ester is performed in an inert solvent consisting essentially of methylene chloride, toluene, pyridine, dimethylformamide, dimethylsulfoxide, N-methylpyrrolidone or hexamethylphosphoric acid, and is performed at a temperature of about −50° to +200° C.

7. A process according to claim 6, wherein $R^4$ is azole-M and the ester is N-alkylated prior to reaction in step (iii).

8. A process according to claim 6, wherein $R^4$ is alkanoyl or aroyl and the ester is reacted with trimethylsilyl cyanide.

9. A process according to claim 1, wherein in step (iv) the reducing agent is tin (II) chloride and hydrochloric acid in an ether solution or is hydrogen and a Raney nickel catalyst.

10. A process according to claim 1, wherein in step (iv) the reducing agent is 2-mercaptoethanol followed by sodium borohydride; sodium hydrothriethoxyaluminate; lithium hydro-triethoxyalanate or diisobutylaluminum hydride.

11. A process according to claim 1, wherein step (v) the organophosphorus compound is a phosphorylide, a phosphonate or a phosphine oxide.

* * * * *